United States Patent
Huang

(10) Patent No.: US 11,298,040 B2
(45) Date of Patent: *Apr. 12, 2022

(54) DEVICE TO REDUCE TRAUMATIC BRAIN INJURY

(71) Applicant: Chiming Huang, Shawnee Mission, KS (US)

(72) Inventor: Chiming Huang, Shawnee Mission, KS (US)

( * ) Notice: Subject to any disclaimer, the term of this patent is extended or adjusted under 35 U.S.C. 154(b) by 639 days.

This patent is subject to a terminal disclaimer.

(21) Appl. No.: 16/223,941

(22) Filed: Dec. 18, 2018

(65) Prior Publication Data

US 2019/0125204 A1    May 2, 2019

Related U.S. Application Data

(63) Continuation of application No. 15/726,095, filed on Oct. 5, 2017, now Pat. No. 10,188,311, which is a
(Continued)

(51) Int. Cl.
| | |
|---|---|
| *A61B 5/00* | (2006.01) |
| *A61B 5/05* | (2021.01) |
| *A61B 5/11* | (2006.01) |
| *A63B 71/10* | (2006.01) |
| *A61B 5/055* | (2006.01) |
| *A42B 3/04* | (2006.01) |

(Continued)

(52) U.S. Cl.
CPC .............. *A61B 5/05* (2013.01); *A42B 3/0473* (2013.01); *A61B 5/055* (2013.01); *A61B 5/11* (2013.01); *A61B 5/1107* (2013.01); *A61B 5/1123* (2013.01); *A61B 5/7282* (2013.01); *A61F 5/3707* (2013.01); *A63B 71/10* (2013.01); *A61B 5/375* (2021.01); *F41H 1/04* (2013.01)

(58) Field of Classification Search
CPC ....... A61B 5/05; A61B 5/1123; A61B 5/7282; A61B 5/11; A61B 5/1107; A61B 5/055; A61B 5/375; A42B 3/0473; A61F 5/3707; A63B 71/10; F41H 1/04
USPC .................................................. 600/587, 595
See application file for complete search history.

(56) References Cited

U.S. PATENT DOCUMENTS

| | | | |
|---|---|---|---|
| 2,820,455 A * | 1/1958 | Hall ........................ | A61F 5/055 602/18 |
| 3,211,768 A | 10/1965 | Considiine | |

(Continued)

*Primary Examiner* — May A Abouelela
(74) *Attorney, Agent, or Firm* — Law Office of Mark Brown, LLC; Christopher M. DeBacker

(57) ABSTRACT

A device for reducing traumatic brain injury comprises a first sensor, a first linkage element, and a processing element. The first sensor is coupled to a head component and configured to measure an acceleration of a user's head and to generate a sequence of real-time measured samples. The first linkage element is configured to connect the head component to a body component and is able to switch between a first state in which it is relatively flexible and a second state in which it is relatively rigid. The first linkage element is switched from its first state to its second state by a locking signal. The processing element is configured to receive the real-time measured samples and to generate the locking signal when each of a portion of the real-time measured samples is greater than one of a corresponding portion of a plurality of dynamic concussion thresholds.

13 Claims, 9 Drawing Sheets

Related U.S. Application Data continuation-in-part of application No. 14/959,083, filed on Dec. 4, 2015, now abandoned.

(60) Provisional application No. 62/088,181, filed on Dec. 5, 2014.

(51) Int. Cl.
  *A61F 5/37* (2006.01)
  *F41H 1/04* (2006.01)
  *A61B 5/375* (2021.01)

(56) References Cited

U.S. PATENT DOCUMENTS

| | | | |
|---|---|---|---|
| 3,387,480 A | 6/1968 | Eaker et al. | |
| 3,645,259 A * | 2/1972 | Schulman | A62B 18/04 128/869 |
| 3,873,996 A * | 4/1975 | Varteressian | A42B 3/0473 2/421 |
| 3,900,896 A * | 8/1975 | Ackerman | A42B 3/0473 2/468 |
| 3,957,040 A * | 5/1976 | Calabrese | A61F 5/055 602/36 |
| 4,219,193 A * | 8/1980 | Newman | A61F 5/055 128/DIG. 23 |
| 4,383,523 A * | 5/1983 | Schurman | A61F 5/055 128/DIG. 23 |
| 4,638,510 A * | 1/1987 | Hubbard | A42B 3/0473 2/6.1 |
| 4,664,341 A * | 5/1987 | Cummings | B64D 25/02 128/857 |
| 4,909,459 A * | 3/1990 | Patterson | A42B 3/0473 2/410 |
| 5,123,408 A * | 6/1992 | Gaines | A42B 3/0473 2/425 |
| 5,158,089 A * | 10/1992 | Swezey | A61B 5/1071 340/573.7 |
| 5,242,377 A * | 9/1993 | Boughner | A61F 5/055 602/17 |
| 5,248,293 A * | 9/1993 | Hubbard | A61F 5/055 128/875 |
| 5,261,125 A * | 11/1993 | Cartwright | A42B 3/0473 2/421 |
| 5,267,708 A * | 12/1993 | Monson | B64D 25/02 244/121 |
| 5,272,770 A * | 12/1993 | Allen | A42B 3/0473 2/421 |
| 5,371,905 A * | 12/1994 | Keim | A42B 3/0473 2/413 |
| 5,425,378 A * | 6/1995 | Swezey | A61B 5/1071 600/587 |
| 5,832,926 A * | 11/1998 | Towlen | A61F 5/055 128/845 |
| 5,919,144 A * | 7/1999 | Bridger | A61B 5/031 600/561 |
| 6,006,368 A * | 12/1999 | Phillips | A42B 3/0473 2/421 |
| 6,052,835 A * | 4/2000 | O'Shea | A42B 3/00 2/425 |
| 6,730,047 B2 * | 5/2004 | Socci | G08B 21/00 600/595 |
| 6,786,877 B2 * | 9/2004 | Foxlin | A61B 5/1114 600/587 |
| 6,968,576 B2 * | 11/2005 | McNeil | A42B 3/0473 2/425 |
| 6,971,123 B2 * | 12/2005 | Weaver | A42B 3/0473 2/411 |
| 7,145,461 B2 * | 12/2006 | Lehrman | A61B 5/0205 340/573.1 |
| 7,155,747 B2 * | 1/2007 | Baker | A42B 3/0473 2/421 |
| 7,371,221 B1 * | 5/2008 | Baker | A61F 5/055 602/18 |
| 7,380,290 B2 * | 6/2008 | Mothaffar | A42B 3/0473 2/421 |
| 7,383,728 B2 * | 6/2008 | Noble | A63B 24/0003 73/379.01 |
| 7,395,558 B2 * | 7/2008 | Mothaffar | A42B 3/0473 2/421 |
| 7,430,767 B2 * | 10/2008 | Nagely | A42B 3/0473 2/425 |
| 7,449,005 B2 * | 11/2008 | Pickering | A61F 5/048 602/18 |
| 7,488,294 B2 * | 2/2009 | Torch | A61B 3/112 600/558 |
| 7,846,525 B2 | 12/2010 | Ghajar | |
| 7,849,525 B2 * | 12/2010 | Ghajar | A42B 3/046 2/416 |
| 7,941,873 B2 * | 5/2011 | Nagely | A63B 71/10 2/425 |
| 8,057,415 B2 * | 11/2011 | Hipp | A61F 5/055 602/18 |
| 8,074,301 B2 * | 12/2011 | Mothaffar | A41D 13/0512 2/468 |
| 8,191,180 B2 * | 6/2012 | Berry | A41D 13/0512 2/468 |
| 8,316,691 B2 * | 11/2012 | Jeftic-Stojanovski | G01D 9/005 73/12.04 |
| 8,316,961 B2 | 11/2012 | Jeftic-Stojanoviski et al. | |
| 8,537,017 B2 * | 9/2013 | Mack | A42B 3/046 340/573.1 |
| 8,548,768 B2 * | 10/2013 | Greenwald | A61B 5/7282 702/141 |
| 8,556,831 B1 * | 10/2013 | Faber | A61B 5/6803 600/587 |
| 8,708,940 B2 * | 4/2014 | Jenkins, III | A61B 5/6803 602/18 |
| 2002/0118121 A1 * | 8/2002 | Lehrman | A61B 5/1117 340/870.16 |
| 2002/0183657 A1 * | 12/2002 | Socci | A42B 3/046 600/595 |
| 2003/0088906 A1 * | 5/2003 | Baker | A42B 3/0473 2/416 |
| 2004/0225236 A1 * | 11/2004 | Wheeler | A61B 5/6814 600/595 |
| 2005/0177929 A1 * | 8/2005 | Greenwald | A61B 5/11 2/425 |
| 2006/0074338 A1 * | 4/2006 | Greenwald | A61B 5/0002 600/549 |
| 2006/0189852 A1 * | 8/2006 | Greenwald | A61B 5/6803 600/300 |
| 2006/0241521 A1 * | 10/2006 | Cohen | A61B 5/1112 600/595 |
| 2006/0270949 A1 * | 11/2006 | Mathie | A61B 5/1117 600/595 |
| 2007/0015611 A1 * | 1/2007 | Noble | G06F 3/016 473/450 |
| 2008/0208013 A1 * | 8/2008 | Zhang | A61B 5/1455 600/301 |
| 2009/0158509 A1 * | 6/2009 | Ghajar | A42B 3/046 2/422 |
| 2010/0198104 A1 * | 8/2010 | Schubert | A61B 5/11 600/558 |
| 2010/0204628 A1 * | 8/2010 | Ghajar | A61F 5/055 602/18 |
| 2010/0263110 A1 * | 10/2010 | Berry | A41D 13/0512 2/459 |
| 2010/0286581 A1 * | 11/2010 | Hipp | A61F 5/055 602/18 |
| 2010/0312145 A1 * | 12/2010 | Ernst | A61B 5/389 600/587 |
| 2011/0184319 A1 * | 7/2011 | Mack | G01L 1/26 600/595 |
| 2011/0184320 A1 * | 7/2011 | Shipps | A42B 3/046 600/595 |

(56) References Cited

U.S. PATENT DOCUMENTS

| | | | |
|---|---|---|---|
| 2011/0219852 A1* | 9/2011 | Kasten | G01L 5/0052 73/12.04 |
| 2011/0288459 A1* | 11/2011 | Jenkins, III | A61B 5/11 602/18 |
| 2012/0174302 A1* | 7/2012 | Jenkins, III | A61B 5/6803 2/468 |
| 2012/0191397 A1* | 7/2012 | Eatwell | A61B 5/11 702/94 |
| 2012/0245439 A1* | 9/2012 | Andre | A61B 5/412 600/310 |
| 2013/0060168 A1* | 3/2013 | Chu | A61B 5/6803 600/595 |
| 2013/0150684 A1* | 6/2013 | Cooner | A61B 5/0261 600/301 |
| 2013/0303946 A1* | 11/2013 | Gettens | A61B 5/11 600/587 |
| 2014/0039355 A1* | 2/2014 | Crisco, III | A61B 5/6803 600/595 |
| 2014/0081180 A1* | 3/2014 | Ghajar | A61B 5/11 600/595 |

* cited by examiner

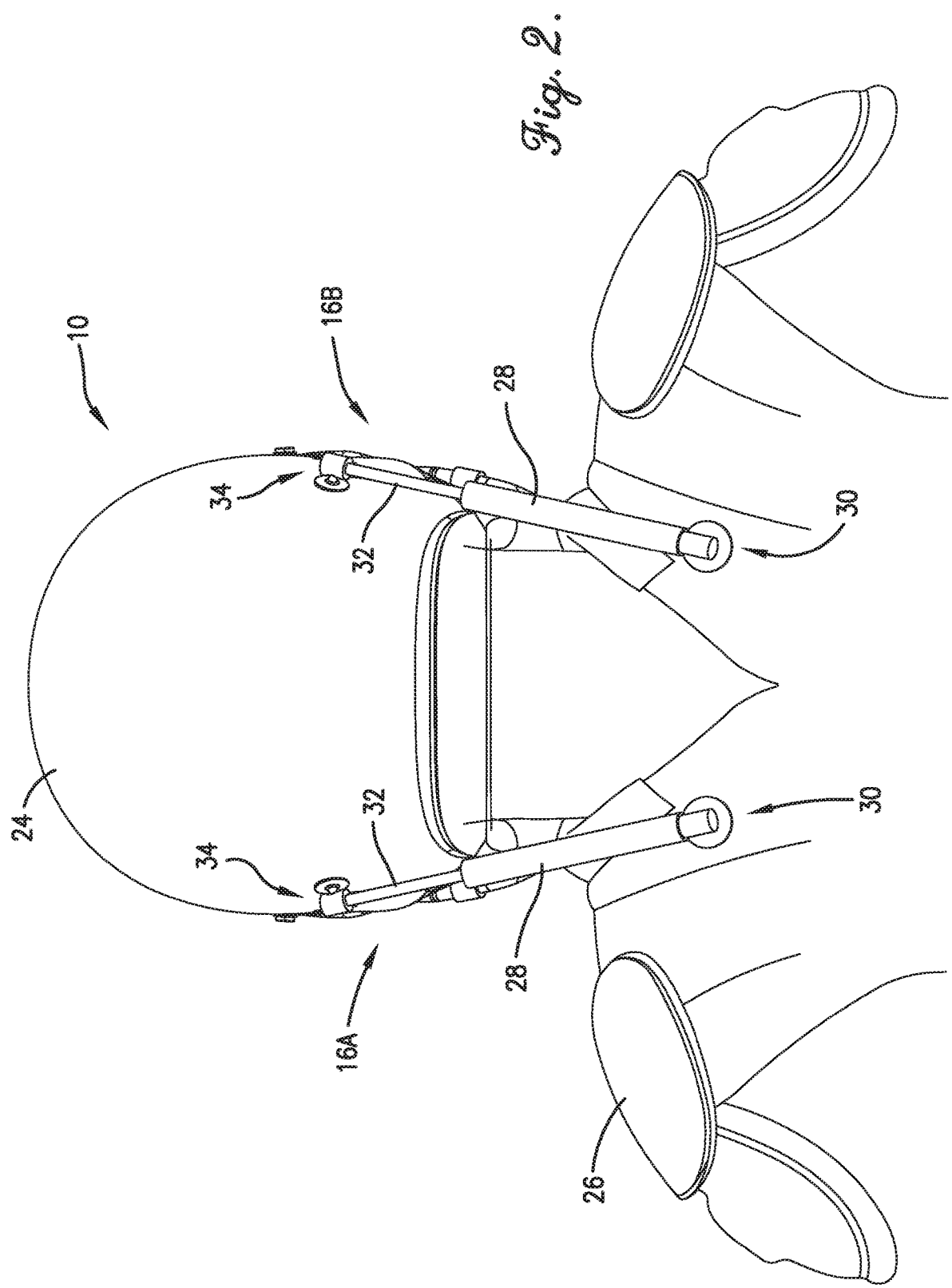

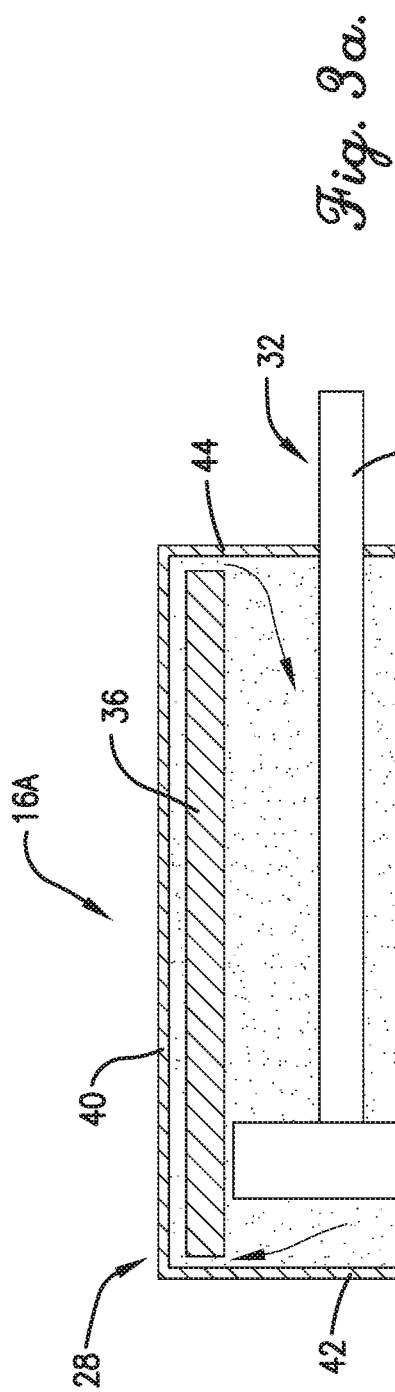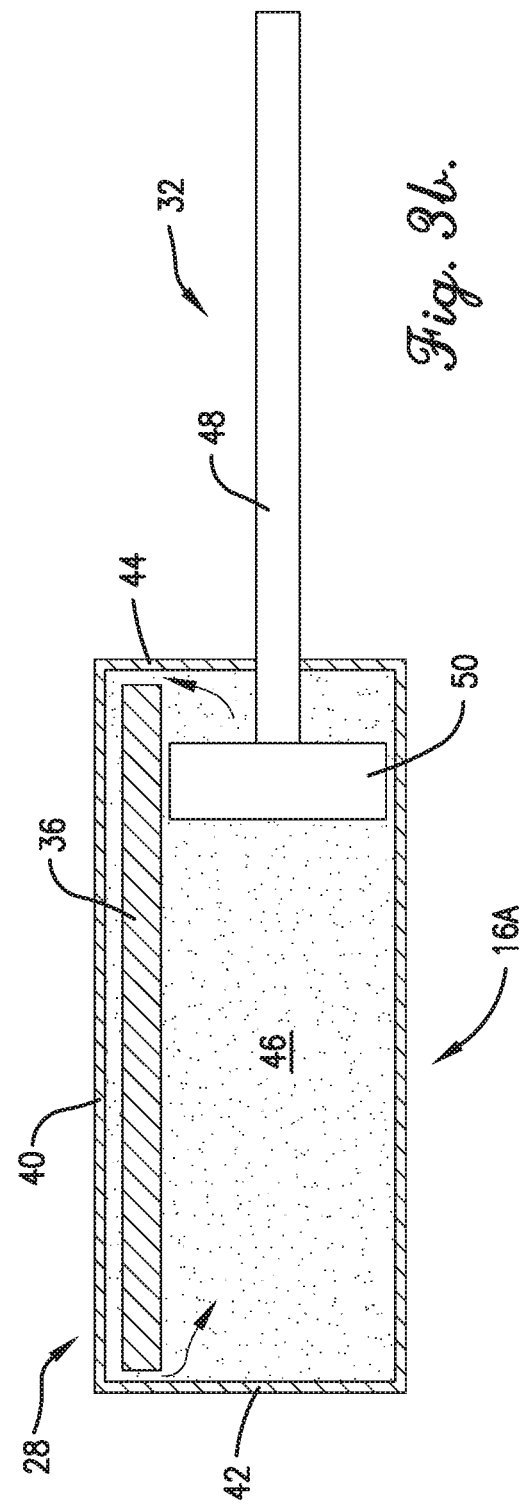

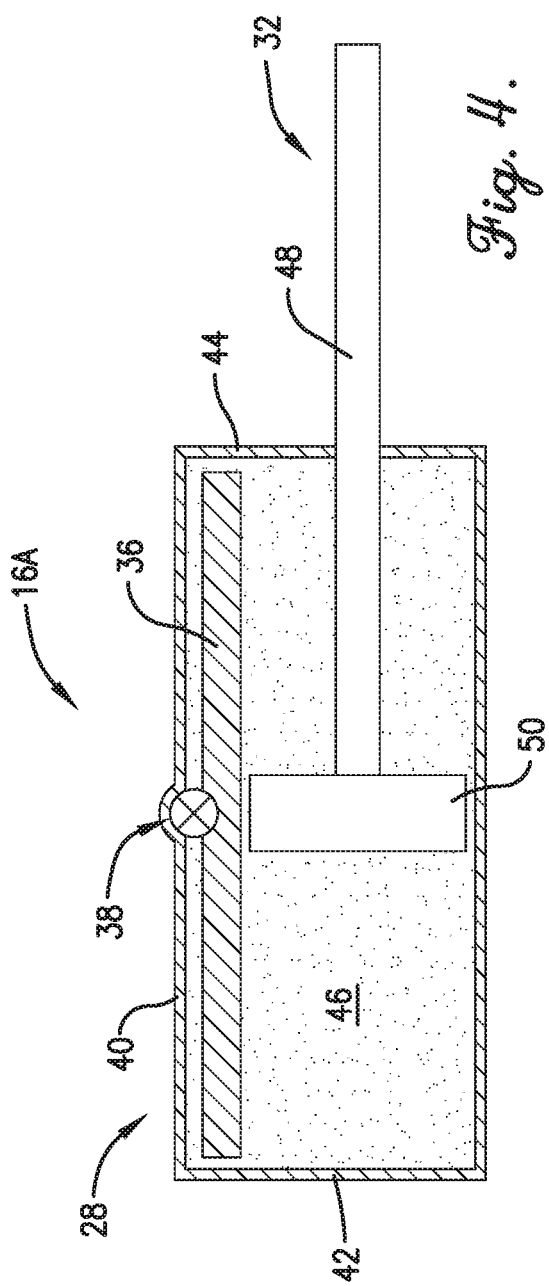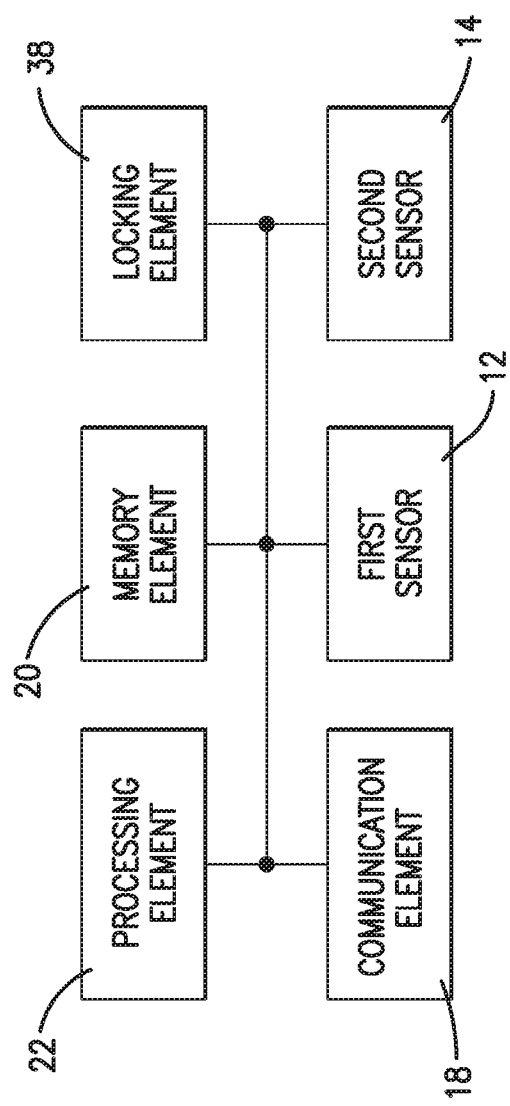

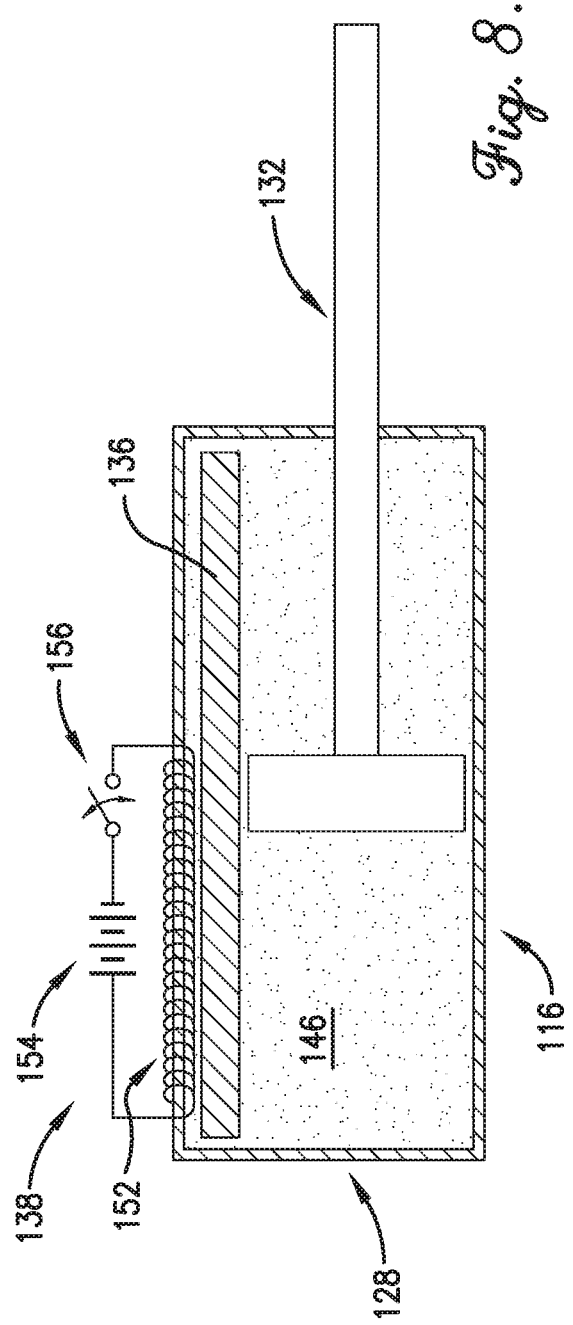
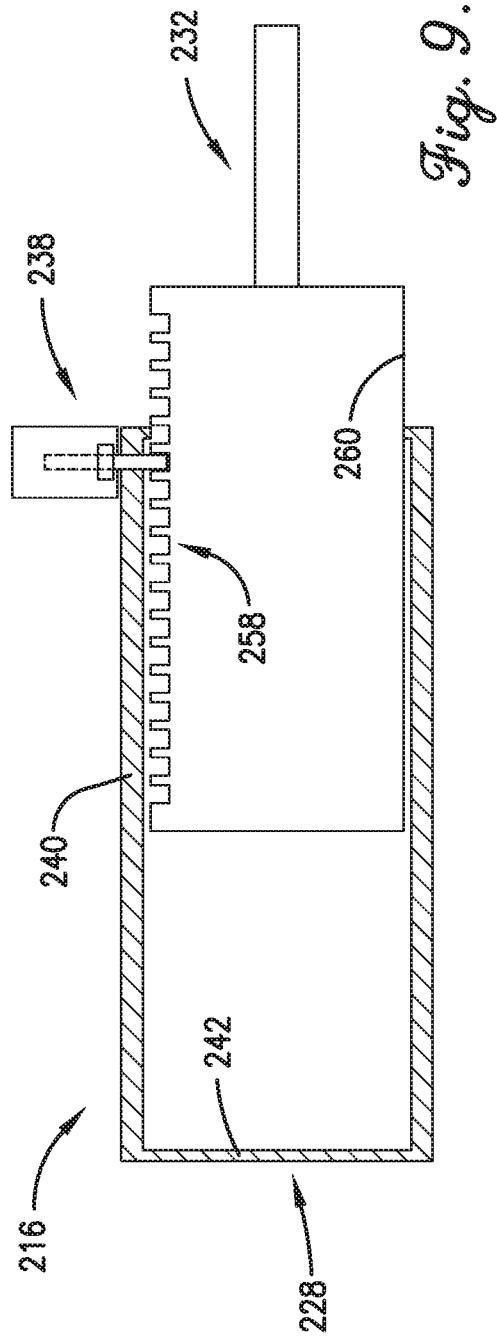

DEVICE TO REDUCE TRAUMATIC BRAIN INJURY

CROSS-REFERENCE TO RELATED APPLICATION

The current patent application is a continuation of U.S. patent application Ser. No. 15/726,095 filed Oct. 5, 2017, which is a continuation-in-part patent application which claims priority benefit with regard to all common subject matter to U.S. patent application Ser. No. 14/959,083, titled "DEVICE TO REDUCE TRAUMATIC BRAIN INJURY", and filed Dec. 4, 2015, that is a non-provisional patent application which claims priority benefit with regard to all common subject matter to U.S. Provisional Patent Application Ser. No. 62/088,181, titled "DEVICE, SYSTEM, AND METHOD TO REDUCE TRAUMATIC BRAIN INJURY: THE SENSOR STAGE", filed Dec. 5, 2014. Both previously-filed applications are hereby incorporated by reference in their entireties into the current patent application.

BACKGROUND OF THE INVENTION

1. Field of the Invention

Embodiments of the current invention relate to devices configured to reduce traumatic brain injury.

2. Description of the Related Art

Closed-head traumatic brain injury (TBI) is typically a result of the brain impacting the interior of the skull. Forces acting on the body or the head generally accelerate the brain. High positive acceleration or negative acceleration may cause the brain to contact the skull with enough force to cause brain injury. In addition, these accelerations set up transient pressure and strain gradients within the soft neuronal tissue of the brain. These gradients can bring about dramatic disruptions in neuronal metabolism and function at the cellular level without obvious or noticeable macroscopic movement of the brain. The types of brain injury may be categorized as blast TBI, concussive TBI, or mild TBI, etc. Blast TBI may be experienced by military or law enforcement personnel while on patrol or traveling in a vehicle. Concussions which are also synonymous with mild TBI or mTBI may be suffered by athletes in sports such as hockey, boxing, or American football. Mild TBI may be experienced by anyone suffering a fall, a vehicular accident, a bicycle accident, or the like.

Systems that have been developed for preventing concussions for players of American football may include one or more acceleration sensors or head-impact-measurement devices coupled to a football helmet and one or more mechanisms connecting the helmet to shoulder pads. The systems may further include a processing element that locks the connecting mechanisms when the acceleration measured by the sensors exceeds a certain constant value believed to be a threshold beyond which a concussion to the player may occur.

In 2017, a detailed review was written by industry experts on the use and effectiveness of head-impact-measurement devices [O'Connor et al, Journal of Athletic Training, 52 (3) 206-227, doi 10.4085/1062-6050.52.2.05]. The authors were from University of Michigan and Virginia Tech and were associated with the HITS (Head Impact Telemetry System, Simbex, Lebanon, N.H., USA) which is widely accepted as the industry standard for head impact sensors. They concluded that, " . . . (such head-impact-measurement devices) did not have the requisite sensitivity (for) . . . concussion. . . . (Such) head-impact-monitoring systems have limited clinical utility due to error rates, designs, and low specificity in predicting concussive injury." This conclusion largely mirrors a series of studies earlier, indicating that data from the HITS lacked sensitivity and specificity and can predict concussion only with a 56% success rate, barely better than coin-toss (these series of studies are cited in the O'Conner et al review).

There may be several reasons for the lack of sensitivity and specificity of the current head-impact-measurement devices. At least one drawback to the approach of sensing head impact in much of the prior art is that the threshold for concussion may be different for different people. In other words, the concussion threshold should be a personal biometric parameter. As an example, an NFL player may endure a hit with an acceleration of 30-60 G (acceleration due to gravity) without injury, whereas the same hit may cause a concussion or other serious injuries in a little league football player. Another drawback is that the threshold for concussion for the same person may be different for different directionalities of the impact force. As an example, if we focus on the same person, he may endure an impact force of 40 G which causes a head rotation in the pitch axis without concussive injury, while he may suffer a concussive injury from an impact force of 35 G which causes a head rotation in the roll axis.

Furthermore, the threshold for an individual may change over time. The period of time may be long and span over many years during which development or maturation occurs in children and adolescents. Or it may be short, spanning over a matter of minutes or days as it is now known that a person is likely to be more vulnerable to a second concussion immediately after a concussion. Or it may be shorter still, spanning over a matter of seconds or fractions of a second as concussions are inopportune events when the impact force catches the head-and-neck when the neck stiffness is low. The matter of time over seconds or less is therefore relevant as the consequences of a head impact event can be disastrous especially when the impact occurs while the person does not know, is not prepared, or is otherwise unaware of the impending impact. Concussive thresholds therefore may be individualized or personalized, may be dependent on the magnitude and directionality of the impact force with respect to the framework of pitch, roll, and yaw axes, and also may be dependent upon the neck stiffness at the moment of impact. All of these factors render it impractical to adopt a certain, one-size-fits-all constant value as a threshold beyond which a concussion may occur or as a threshold beyond which some form of protective countermeasure should be launched.

Recent literature data strongly suggest that while concussions may lead to long-term neurological deficits as depicted by chronic traumatic encephalopathy (CTE), repetitive sub-concussive impact events may account for even more cases of CTE than concussive impact events. Therefore, another drawback to the current approach is that sensors in many prior arts do not provide any information or data to help track and subsequently manage harmful, sub-concussive impact events.

Another drawback to the current approach is that sensors in many prior arts are programmed with an emphasis to sample the peak amplitudes of the impact force/energy, typically requiring more than 10-20 ms to manifest. Based on image analysis of high-speed videos carried out in the inventor's laboratory, a concussion in the form of a knockout in boxing matches may take place within 30 ms after impact in boxers (not yet published). The time window between sensing a potentially concussive impact and launching a countermeasure is therefore measured in ms. Many of the current approach of sensing impact force/energy do not consider the essence of speed and may be therefore too slow to be incorporated in a device designed for launching an effective countermeasure to prevent a concussion before such a concussion or related brain injuries can take effect.

SUMMARY OF THE INVENTION

Embodiments of the current invention solve the above-mentioned problems by directly addressing some of the drawbacks. First, the sensor stage or the smart head-impact-monitoring system of the present invention identifies a dynamic concussion threshold that is individualized or custom-fit to the user by machine-learning the normal, non-injurious head movement parameters (e.g. head accelerations, velocities, etc.) of the individual user and thereby relevant information on the three-dimensional biomechanical properties of the head-and-neck of the user (about the pitch, roll, and yaw axes), whether the user is a child, adolescent, or adult. The data or knowledge that is learned is stored in the memory element of the smart head-impact-monitoring system of the present invention and is retrieved for decision-making purposes analogous to how chess-playing computers with artificial intelligence (AI) make use of moves made by previous players. Second, a prototype of the sensor stage or the smart head-impact-monitoring system of the present invention was fabricated and tested in the inventor's laboratory. When the algorithm of pitch, roll, and yaw analysis or an organization of data on movement parameters (velocities, accelerations, etc.) about the pitch, roll, and yaw axes was introduced in our video analysis, the team of the inventor's laboratory obtained a >95% success rate in "predicting" concussions based on movement parameters (results yet unpublished) by using Student's t-tests. Third, the processing element of the present invention helps us to acquire population data on the normal, non-injurious head movement parameters (e.g. head accelerations, velocities, etc.). From this database, the present invention can help to track potentially harmful, sub-concussive head impact events. Fourth, the sensor stage or the smart head-impact-monitoring system of the present invention monitors the neck stiffness of the user in real time and is able to dispense the most protection when the neck is the least stiff. Fifth, once a potentially injurious head impact event is detected by the sensor stage or the smart head-impact-monitoring system of the present invention, the present invention also provides methods and devices that are utilized with head gear and body wear to dissipate the impact force and energy and reduce traumatic brain injury before such injury can occur.

A first embodiment of the current invention provides a device for reducing traumatic brain injury and broadly comprises a first sensor, a first linkage element, and a processing element. The first sensor is coupled to a head component and configured to measure an acceleration of a user's head as a result of motion of the head component and to generate a sequence of real-time measured samples. The first linkage element is configured to connect the head component to a body component and is able to switch between a first state in which it is relatively flexible and a second state in which it is relatively rigid so that an impedance-preferred pathway is established for impact energy dissipation away from the head and toward the body or the trunk of the user. The first linkage element is switched from its first state to its second state by a locking signal which is generated by a processing element after the impact but before the impact energy can cause a concussion. The processing element is configured to receive the real-time measured samples on head motion from the first sensor and to generate the locking signal when each of a portion of the real-time measured samples is greater than one of a corresponding portion of a plurality of dynamic concussion thresholds.

Part of the inventor's laboratory research has indicated that a concussion can manifest within 30 milliseconds after the impact. The actions of the processing element and the linkage elements are therefore rendered within a time period measured in milliseconds and not longer than 20 milliseconds.

A second embodiment of the current invention provides a system for reducing traumatic brain injury and comprises a first sensor and a second sensor, a first linkage element, and a processing element. The first sensor is coupled to a head component and configured to measure an acceleration of a user's head as a result of motion of the head component and to generate a sequence of real-time measured samples. The second sensor is coupled to a body component and configured to measure an acceleration of a user's body as a result of motion of the body component and to generate a sequence of real-time measured samples. Together, the first sensor and the second sensor yield data on the dynamic neck stiffness of the user, which is used in conjunction with the dynamic concussion threshold in order to forecast whether a certain impact may cause an imminent concussive injury to the user. In this way, the present invention can render more protection when the neck is less stiff, and render the most protection when the neck is the least stiff.

The first linkage element is configured to connect the head component to a body component and is able to switch between a first state in which it is relatively flexible and a second state in which it is relatively rigid so that an impedance-preferred pathway is established for impact energy dissipation away from the head and toward the body of the user. The first linkage element is switched from its first state to its second state by a locking signal which is generated by the processing element after the impact but before the impact energy can cause brain injury. The processing element is configured to receive the real-time measured samples from the first sensor and the second sensor and determine a period of motion which includes the real-time measured samples whose value is greater than a motion threshold. Having thus the capacity of recognizing and identifying individual head movement as discrete events, the processing element may determine and thus machine-learn a profile on normal, voluntary, non-injurious, and non-concussion-inducing movement of the head and the body of the individual user based on a plurality of biomechanical parameters (head velocities, accelerations, etc.). At a functional level, these profiles are effectively representations of the three-dimension biomechanical properties of the user's head-and-neck. Because the biomechanical properties of the head-and-neck of each user are different and individualized, the profile on normal, voluntary, non-injurious, and non-concussion-inducing movement of the head and the body of each user is different and individualized. The processing element may further compute sequential dynamic concussion thresholds from the profile on normal, voluntary, non-injurious, and non-concussion-inducing movement of the head and the body of the individual user. The resultant dynamic concussion thresholds are also different and individualized. The processing element may further compare, in sequential order, each of the real-time measured samples in the period of motion with the corresponding dynamic concussion thresholds. The processing element may also compute a dynamic neck stiffness index by monitoring the data from first sensor and the second sensor. During the data analysis, the steps of data analysis are designed to focus on the components of forces or head accelerations as well as the dynamic neck stiffness index in the pitch, roll, and yaw axes.

A third embodiment of the current invention provides a method of reducing traumatic brain injury comprising the steps of: receiving a sequence of real-time measured samples from a first sensor coupled to a head component, determining a period of motion which includes the real-time measured samples whose value is greater than a motion threshold, calculating a dynamic concussion threshold for each of a plurality of sequential time-based profile cells, comparing, in sequential order, each of the real-time measured samples in the period of motion with the corresponding dynamic concussion threshold, and generating a locking signal if necessary. In other words or more specifically, we (1) monitor head accelerations of the user in pitch, roll, and yaw axes in real time, (2) machine-learn the normal, non-injurious head movement parameters (e.g. accelerations, velocities, etc.) of the user, (3) use these parameters to define the boundaries between non-injurious and potentially injurious head movements, (4) use these boundaries to set personalized injury thresholds by determining when the head movement parameters of an impact are outside the normal and non-injurious range and may cause injury. During the data analysis, the steps of data analysis are designed to focus on the components of forces or head accelerations in the pitch, roll, and yaw axes.

There are several reasons why it is important that the steps of data analysis in the current invention focus on the components of forces or head accelerations in the pitch, roll, and yaw axes. First, in the 2017 review article, MEMS hardware and software, including the sophisticated Head Impact Telemetry System or HITS, used by Riddell, have so far failed to predict concussions with sufficient sensitivity and specificity. Second, in the inventor's lab, when data analysis was carried out with a focus on the components of forces or head accelerations in the pitch, roll, and yaw axes, we are able to predict concussions at the p=0.01 level. (At present, this result has not been published but we will present more detailed data later in the application.)

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein:

FIG. 2 is a rear elevational view of the device of FIG. 1;

FIG. 3a is a sectional view of a first linkage element, the first linkage element including a first member, a second member, a bypass element, and a fluid medium, wherein FIG. 3a depicts the second member telescoping in to the first member and moving the fluid medium in a first direction;

FIG. 3b is a sectional view of the first linkage element, wherein FIG. 3b depicts the second member telescoping out of the first member and moving the fluid medium in a second direction, opposite of the first direction;

FIG. 4 is a sectional view of the first linkage element, the first linkage element further including a locking element;

FIG. 5 is a schematic block diagram of at least some of the electronic components of the device of FIG. 1;

FIG. 8 is a sectional view of a second embodiment of the first linkage element;

FIG. 9 is a sectional view of a third embodiment of the first linkage element;

Figure 1:
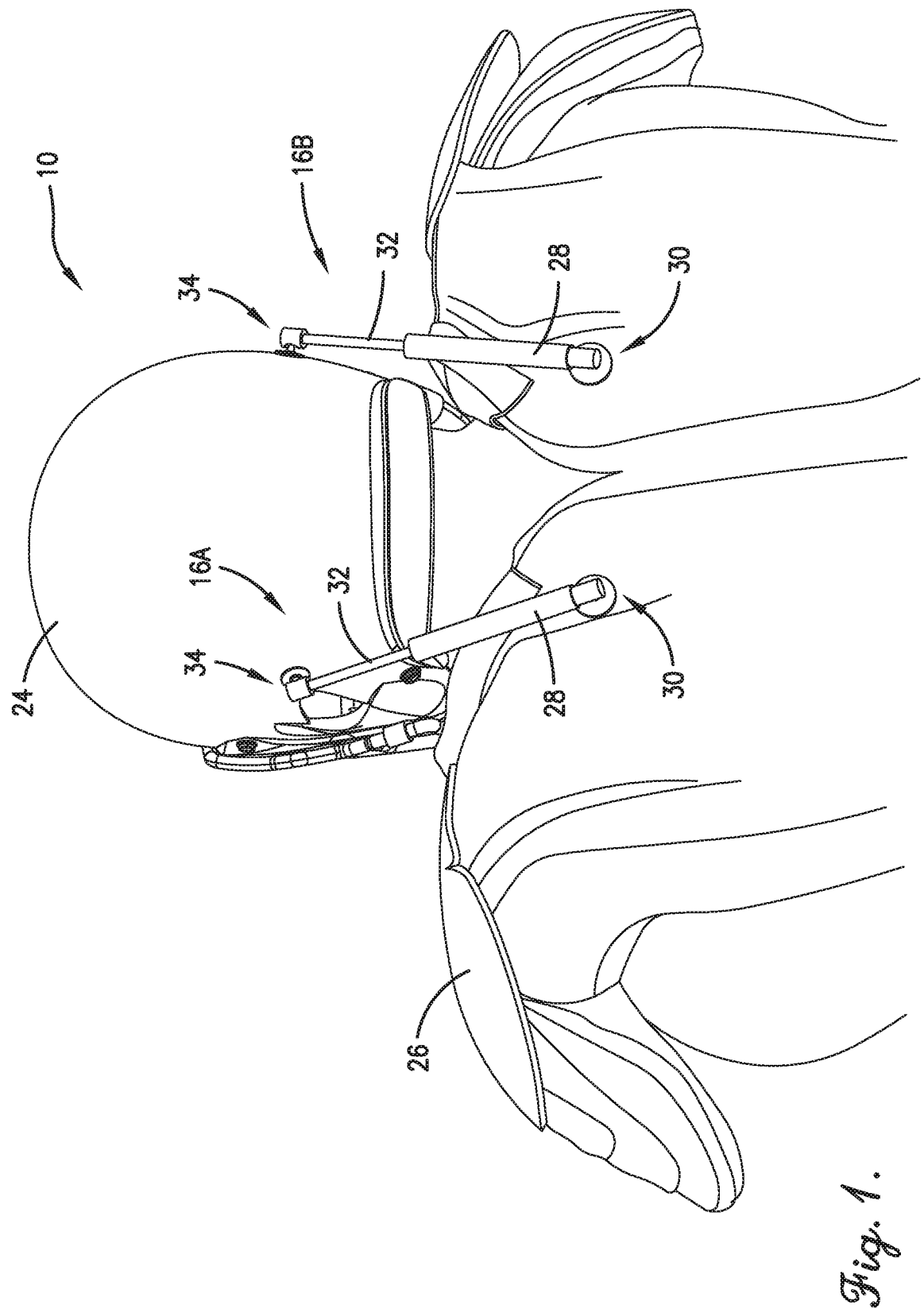
FIG. 1 is a perspective view of a device, seen from the rear, for reducing traumatic brain injury constructed in accordance with a first embodiment of the current invention and utilized with an American football helmet and shoulder pads, the device including first and second sensors and first and second linkage elements.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

A device 10 for reducing traumatic brain injury constructed in accordance with a first embodiment of the current invention is shown in FIGS. 1, 2, and 5 and broadly comprises a first sensor 12, a second sensor 14, a first linkage element 16A, a second linkage element 16B, a communication element 18, a memory element 20, and a processing element 22. The device 10 may be utilized by a user engaging in activity during which a concussion may possibly be caused by an impact to the head or to the body. The activity may include contact sports such as hockey, boxing, American football, soccer, snow or ice-related sports such as skiing, snowboarding, sledding, sports in which falling or landing on the head is possible such as skateboarding, bicycling, equestrian activities, motorcycle riding, automobile driving, also including military combat, and the like. In a typical usage scenario for the current invention, the device 10 may interface with equipment worn on the head or the body including a head component 24 or apparatus, such as a helmet or other headgear, and a body component 26 or apparatus, such as the shoulder pads in American football or the body armor worn by soldiers in combat.

In some embodiments, the linkage elements 16A, 16B may be omitted for the purpose of and as a tool for objective and quantitative diagnosis for concussive brain injuries with high sensitivity and specificity.

The first sensor 12, indicated in FIG. 5, generally measures linear as well as rotational motion of the user's head. The term "sensor" may include a plurality of sensors or types of sensors. Thus, the first sensor 12 may include motion sensors, velocity sensors, shock sensors, accelerometers, gyroscope chips, magnetometer chips, inclinometers, angle rate sensors, angular velocity sensors, vibration sensors, binary force switches, or the like, or combinations thereof. The first sensor 12 may include technology such as strain gauges, piezoelectric elements, micro electro-mechanical systems (MEMS), nanotechnologies in which a material, solid or liquid, can change its stiffness while modulated by electromagnetic fields, or the like, or combinations thereof. The first sensor 12 may measure linear position, velocity, acceleration, or force along a single axis or multiple axes, such as any three mutually orthogonal axes, e.g., the X, Y, Z axes, and may record, communicate, or output a sensor measurement. Each sensor measurement may include a plurality of values from a plurality of sensors which may be in the form of vector data or magnitude data. Thus, in various embodiments, the first sensor 12 may generate three or more values for the three linear measurements. In addition or instead, the first sensor 12 may measure angular or rotational position, velocity, acceleration, or force concerning head movement along or about mutually orthogonal axes, such as pitch, roll, and yaw. The second sensor 14 may measure angular or rotational position, velocity, acceleration, or force concerning body movements along mutually orthogonal axes, such as front-to-back, left-to-right, and up-and-down. With regard to measuring the acceleration of the head, pitch is nodding to gesture yes, roll is bending the head-and-neck toward one or the other shoulder, and yaw is gesturing no or turning the head to watch cars from both directions before crossing a street. Accordingly, the first sensor 12 may generate three or more values for the three angular measurements.

The sensor measurements may be an analog value, a digital value, a pulse-width modulation (PWM) value, or the like. An exemplary first sensor 12 may output the sensor measurements as real-time measured samples at an exemplary frequency ranging from 500 hertz (Hz) to 20 kilohertz (kHz) or higher. This range of frequencies should be great enough to detect an impulse-like impact, whose duration may range from a fraction of a millisecond (ms) to single and up to double digits of milliseconds. The first sensor 12 may also include electronic circuitry such as amplifiers, analog-to-digital converters (ADCs), or other conversion circuits.

The first sensor 12 may be positioned within the interior of the head component 24. The head component 24 may be headwear, headgear, a helmet, such as a sports helmet, a motorcycle or automobile helmet, or a combat helmet, or the like. In some embodiments, the first sensor 12 may further include first and second resilient members, such as springs, that are coupled to opposing sides of the first sensor 12. The first resilient member may contact an inner surface of the head component 24, and the second resilient member may contact the user's head. In other embodiments, the first sensor 12, with or without resilient members, may be coupled to padding on the interior of the head component 24, or coupled to a hard shell of the head component 24, such that when the head component 24 is worn, the first sensor 12 may contact the user's head in order to detect motion, force, and other physical parameters related to the force applied to the head or the helmet. It may be advantageous for the first sensor 12 to also measure the force at the helmet, which is typically of a greater magnitude than the force at the head.

Alternatively, the sensor stage or the smart head-impact-monitoring system of the present invention can be deployed without a head component 24, a body component 26, a first linkage element 16A, and a second linkage element 16B. In this configuration, such as in soccer players, the first sensor 12 may also be integrated into a head-band or a skull-cap or other wearable fabric in order to allow the sensing of head movement and accelerations.

The second sensor 14, indicated in FIG. 5, may be substantially similar to the first sensor 12 in structure and function. The second sensor 14 may be positioned on the body component 26 and may measure motion of the user's body. Alternatively, the second sensor 14 may be affixed directly to the back of the user via an adhesive element just below the base of the neck. Thus, the second sensor 14 may generate data based on the motion of the user's body, particularly the user's upper body (as oppose to limb movements). In the present invention, information on the user is acquired via the first sensor 12 and the second sensor 14. In other embodiments, more than two sensors may be deployed and information on the user may be acquired via a system of sensors.

We now summarize the description up to this point, which covers the overall design of the device 10 and the multiple sensors employed by the device 10. In the present invention, the first sensor 12 and the second sensor 14 make measurement of the movement parameters of the head and the body of the user. The data may include measurements of position or distance, orientation, velocity, and acceleration. The main objective of employing multiple sensors is to obtain data or information on dynamic parameters of the user's body.

The first linkage element 16, as seen in FIGS. 1-4, generally provides a link between the user's head and the user's body that is normally flexible but becomes rigid upon receiving a locking signal from processing element 22 as a result of an impact to the head or the body that could potentially cause a concussion. The first linkage element 16 may include a first member 28, a first end joint 30, a second member 32, a second end joint 34, a bypass element 36, and a locking element 38.

The first member 28 may be of generally hollow, cylindrical or tubular construction and may include a chamber defined by a circumferential sidewall 40, a first end wall 42 connected to one end thereof, and a second end wall 44 connected to the opposing end thereof. The first end wall 42 may be generally disc shaped. The second end wall 44 may be generally disc shaped with a circular opening in the center thereof. The first member 28 may further include a fluid medium 46 housed within the chamber. The fluid medium 46 may include liquids, such as hydraulic fluids (including water), or gases, such as atmospheric air.

The first end joint 30, seen in FIGS. 1 and 2, may connect the first member 28 to the body component 26 and may include a universal joint with a first connector coupled to the sidewall 40 or the first end wall 42 of the first member 28 and a second connector coupled to the body component 26 in a location corresponding to the left side of the upper back of the user. The universal joint may provide rotation about three orthogonal axes such that the first member 28 may freely rotate in any direction with respect to the body component 26.

The second member 32 may include a plunger with an elongated rod 48 and a disc 50 connected to one end thereof. The disc 50 may be positioned within the chamber of the first member 28, and the rod 48 may extend through the opening in the second end wall 44 of the first member 28. During operation of the device 10, discussed in more detail below, the second member 32 may travel or slide axially within the first member 28 in a telescoping fashion. Both the rod 48 and the disc 50 may contact and interact with the fluid medium 46.

The second end joint 34, seen in FIGS. 1 and 2, may be similar in structure and function to the first end joint 30. The second end joint 34 may include a first connector coupled to the rod 48 of the second member 32 and a second connector coupled to the head component 24 on one side thereof, corresponding to the left side of the user's head. The second end joint 34 may provide rotation about three orthogonal axes such that the second member 32 may freely rotate in any direction with respect to the head component 24.

The bypass element 36 generally provides a path for the fluid medium 46 of the first member 28 to recirculate. The bypass element 36 may include a chamber, a first port positioned at one end of the chamber, and a second port positioned at an opposing end of the chamber. The first and second ports may each provide fluid access to the chamber. The first port may be coupled to the first member 28 at, or near, the first end wall 42, while the second port may be coupled to the first member 28 at, or near, the second end wall 44. In some embodiments, the bypass element 36 may be positioned adjacent to the first member 28. In other embodiments, the bypass element 36 may have a cylindrical shape that forms a chamber surrounding the first member 28.

When the rod 48 of the second member 32 is free to travel or slide axially with respect to the first member 28, the linkage element 16 may change its length, thereby allowing the head component 24 to move freely relative to the body component 26. Under this condition, the linkage element 16 is said to be in a flexible state.

The locking element 38, seen in FIG. 4, generally is capable to change the state of the linkage element 16 from flexible to rigid and may include devices, such as solenoid valves with solenoids that deliver a mechanical action when provided with an electronic signal. The locking element 38 may be coupled to the bypass element 36 and may function as a valve which stops the flow of the fluid medium 46 through the bypass element 36 when it receives a locking signal from the processing element 22. The locking element 38 may include components that interact or function with hydraulic or pneumatic systems. In an exemplary embodiment, the locking element 38 may include a solenoid valve with a movable core or plunger that can be extended from and retracted into a body. The solenoid valve may be attached to the bypass element 36 in series such that the solenoid valve may stop the flow of the fluid medium 46 by ejecting a core element within the chamber of the solenoid valve and into the flowing path of the fluid medium 46. In other words, when the locking element 38 receives the locking signal, the core of a solenoid valve may be ejected into the flowing path of fluid medium 46 within the chamber of the bypass element 36 such that it completely blocks the path of the fluid medium 46, stopping the flow thereof.

When the flow of the fluid medium 46 is stopped, the rod 48 of the second member 32 is no longer free to travel or slide axially with respect to the first member 28, the linkage element 16 may not change its length, thereby preventing the head component 24 from moving freely relative to the body component 26. Under this condition, the linkage element 16 is said to be in a rigid state.

The first linkage element 16 may function as follows. In the flexible state, given the connection of the first linkage element 16 to the head component 24 and the body component 26, every time the user moves his head the second member 32 may telescope, or piston, in and out of the first member 28. While the second member 32 is moving inward as seen in FIG. 3a, the disc 50 may push the fluid medium 46 toward the first end wall 42. The fluid medium 46 may exit the first member 28 through the first port of the bypass element 36, travel through the chamber, and enter the first member 28 again through the second port of the bypass element 36 proximal to the second end wall 44. While the second member 32 is moving outward as seen in FIG. 3b, the process may reverse, with the fluid medium 46 flowing in the opposite direction, such that the disc 50 may push the fluid medium 46 toward the second end wall 44. The fluid medium 46 may exit the first member 28 through the second port of the bypass element 36, travel through the chamber, and enter the first member 28 again through the first port of the bypass element 36 proximal to the first end wall 42. As long as the locking element 38 is not activated or energized, the fluid medium 46 may flow freely through the chambers of the first member 28 and the bypass element 36. In the flexible state, therefore, the length of the linkage element 16 is free to change and the head element 24 is free to move relative to the body element 26.

In the rigid state, the locking element 38 is energized, preventing the flow of the fluid medium 46 through both the chamber of the first member 28 and the chamber of the bypass element 36. When the fluid medium 46 does not flow, the second member 32 may not move with respect to the first member 28—effectively locking or holding constant the length of the linkage element 16. In the rigid state, therefore, the length of the linkage element 16 (i.e. 16A, 16B) is fixed and not free to change, the head element 24 is not free to move relative to the body element 26.

The second linkage element 16B, as seen in FIGS. 1 and 2, may be substantially similar to the first linkage element 16A in structure and function and may include the same components discussed above. The first end joint 30 of the second linkage element 16B may be coupled to the body component 26 in a location corresponding to the right side of the upper back of the user. The second end joint 34 of the second linkage element 16B may be coupled to the head component 24 on one side thereof, corresponding to the right side of the user's head. The second linkage element 16B may operate in combination with the first linkage element 16A to prevent movement of the head with respect to the body when a potentially injurious impact to the head or body is detected.

We now summarize the description up to this point, which covers a major working principle of the present invention—to quickly and significantly increase the effective dynamic neck stiffness of the user during a head impact event. The processing element 22 of the sensor stage accomplishes this task by issuing a locking signal activating the linkage elements. The linkage elements 16A and 16B may change from a flexible state that does allow head movements to a rigid state that does not allow head movements. As many concussions occur as the impact force catches the head-and-neck in a state of low neck stiffness. In the rigid state, linkage element 16A and 16B provide a significant increase in the dynamic neck stiffness of the user. Moreover, in the rigid state, linkage element 16A and 16B provide an inflexible and impedance-preferred pathway for the efficient dissipation of impact energy. Therefore, when the linkage elements 16A and 16B are in the rigid state, the impact energy is channeled and dissipated to the trunk or the body and is not able to cause brain injury. A practical consideration is that the actions of the linkage elements 16A and 16B must be on-line, or the linkage elements 16A and 16B must switch from a flexible state to a rigid state, within a time window that is after the moment of impact but is before brain injury can occur. The inventor's lab has determined that this time window is no more than 10-20 ms. The mechanisms activating the linkage elements 16A and 16B, therefore, may be provided by fast technology that may involve miniaturized solenoid valves and the like. Based on the processing time of sensors and processing elements and the response speed of associated and additional mechanical components such as valves, the overall response time of the linkage elements is estimated generally in single digit of milliseconds (ms).

The communication element 18, indicated in FIG. 5, generally allows communication with external systems or devices. The communication element 18 may include signal or data transmitting and receiving circuits, such as antennas, amplifiers, filters, mixers, oscillators, digital signal processors (DSPs), and the like. The communication element 18 may establish wireless communication by utilizing radio frequency (RF) signals and/or data that comply with communication standards such as cellular 2G, 3G, or 4G, Institute of Electrical and Electronics Engineers (IEEE) 802.11 standard such as WiFi, IEEE 802.16 standard such as WiMAX, Bluetooth™, or combinations thereof. In addition, the communication element 18 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 18 may establish communication through connectors or couplers that receive metal conductor wires or cables which are compatible with networking technologies such as ethernet. In certain embodiments, the communication element 18 may also couple with optical fiber cables. The communication element 18 may be in communication with the processing element 22 and the memory element 20.

The memory element 20, indicated in FIG. 5, may include electronic hardware data storage components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 20 may be embedded in, or packaged in the same package as, the processing element 22. The memory element 20 may include, or may constitute, a "computer-readable medium". The memory element 20 may store the instructions, code, code segments, software, firmware, programs, applications, apps, services, daemons, or the like that are executed by the processing element 22. The memory element 20 may also store settings, data, documents, sound files, photographs, movies, images, databases, and the like.

The processing element 22, indicated in FIG. 5, may include electronic hardware components such as processors, microprocessors (single-core and multi-core), microcontrollers, digital signal processors (DSPs), field-programmable gate arrays (FPGAs), analog and/or digital application-specific integrated circuits (ASICs), or the like, or combinations thereof. The processing element 22 may generally execute, process, or run instructions, code, code segments, software, firmware, programs, applications, apps, processes, services, daemons, or the like. The processing element 22 may also include hardware components such as finite-state machines, sequential and combinational logic, and other electronic circuits that can perform the functions necessary for the operation of the current invention. The processing element 22 may be in electronic communication with the other electronic components through serial or parallel links that include address busses, data busses, control lines, and the like.

The processing element 22 may receive data from the first sensor 12 and the second sensor 14 on the user's head movement or body movement. The data may include measurements of position or distance, orientation, velocity, and acceleration. Alternatively, these parameters may be derived from the first and second sensors 12 and 14. The processing element 22 may be operable to, configured to, or programmed to utilize the data to generate a profile of one or more of the above-mentioned parameters on the user's head movement or body movement as described below. In various embodiments, the processing element 22 may be programmed to generate a profile for each one of the parameters, resulting in a position profile, an orientation profile, a velocity profile, and an acceleration profile, and so on. In addition, there may be a profile for each parameter from each of the first and second sensors 12, 14. These profiles may offer a description on the range, the mean value, and the variation concerning the user's normal, non-injurious, and non-concussion-inducing head movement or body movement. These descriptions, data analysis, and the profiles on the normal, non-injurious head movement parameters may offer a further description on the boundaries of what the head-and-neck of the user can normally tolerate without danger of injury. These boundaries may include details of head rotations about the pitch, roll, and yaw axes. Each profile may further include a plurality of sequential time-based cells, or an array, for the given parameter, wherein each cell includes information on the statistics from data collected over an extended period. Thus, the data may include a first cell associated with a first sample time period, wherein the first time sample period is the time when the processing element 22 determines that motion has begun, which is discussed in more detail below. Stored in the first cell may be a plurality of historically captured motion values, one motion value (such as velocity, acceleration, etc., or combinations thereof) for each occasion when the user began going into motion. Additionally, or alternatively, stored in the first cell may be a plurality of statistical values, such as the mean, the standard deviation, the median, the range of values, the minimum value, the maximum value, etc. for all of the historically captured motion values. A second cell of the profile may be associated with a second sample time period and may include a plurality of motion values historically captured during a second sample time period after the processing element 22 had determined that motion of the user had begun. Additionally, or alternatively, the second cell may include a plurality of statistical values for all of the historically captured motion values, similar to the first cell. Likewise, each of the remaining cells of the profile may include historically captured motion values for the associated sample time period, statistical data on the historically captured motion values, or combinations thereof. The profile may include thousands to hundreds of thousands, or more, cells.

In summary, such information constitutes a detailed and historical profile of the personal data on the user's normal, non-injurious, and non-concussion-inducing head movement or body movement collected over an extend period, e.g. days, weeks, months, or even longer.

The profile is typically created with the device 10 in a calibration mode by having the user wear the device 10 while he engages in normal activity that avoids receiving any significant impacts that may lead to concussive injuries. For example, if the user is playing American football, he may wear the head component 24, such as a football helmet, and the body component 26, such as shoulder pads. The other components of the device 10, such as the first sensor 12, the second sensor 14, and the first and second linkage elements 16A, 16B may be connected as discussed above. The user may play or practice football, kicking or punting the ball, running with the ball, throwing and catching passes, blocking or being tackled, etc. All the while, the user may execute normal, voluntary, non-injurious, and non-concussion-inducing head movement or body movement. And, all the while, the first and second sensors 12, 14 are transmitting measured data on the user's normal, voluntary, non-injurious, and non-concussion-inducing head movement or body movement to the processing element 22. In some instances, the data may be first stored in the memory element 20. Specifically, each time, instance, or occurrence that the processing element 22 determines that motion has begun, motion values (such as velocity, acceleration, etc., or combinations thereof) received from the first sensor 12 and/or the second sensor 14 may be stored in the profile which is stored in the memory element 20. Furthermore, the first motion value received after the processing element 22 has determined that motion has begun may be stored in, and/or used to create statistical data in, the first cell of the profile. The second motion value received may be stored in, and/or used to create statistical data in, the second cell of the profile, and so forth for successive motion values and cells of the profile.

The profile may also be created without some of the components in device 10 (such as a head component 24, a body component 26, a first linkage element 16A, and a second linkage element 16B), as long as the sensor stage or the smart head-impact-monitoring system of the present invention (including a first sensor 12, a second sensor 14, a communication element 18, a memory element 20, and a processing element 22) is in a calibration mode. This can be accomplished by having the user wear the sensor stage or the smart head-impact-monitoring system (e.g. as part of a head-band or a skull-cap) while he engages in normal activity such as playing soccer, riding a bicycle. All the while, the user may execute normal, voluntary, non-injurious, and non-concussion-inducing head movement or body movement. And, all the while, the first and second sensors 12, 14 are transmitting measured data on the user's normal, voluntary, non-injurious, and non-concussion-inducing head movement or body movement to the processing element 22. In some instances, the data may be first stored in the memory element 20.

We now summarize the description up to this point, which covers a major working principle of the present invention— to define and measure an individualized or personalized concussion threshold by dedicating the sensor stage in the present invention to a single user with the sensor stage broadly comprises of sensor 12, sensor 14 and their associated communication element 18, memory element 20, and processing element 22. The dedicated sensor stage further accomplishes this task by first defining, measuring, and compiling a statistical profile of the user's normal, non-injurious head movements in the calibration mode while laying the foundation for the subsequent derivation of an individualized or personalized concussion threshold (for details, see later). In other words, the calibration mode allows the sensor stage or the smart head-impact-monitoring system of the present invention to build a series of profiles on the normal, non-injurious, head movements of the user via machine learning. The profiles are defined by measurements of position or distance, orientation, velocity, and acceleration on the head movements of the user. In turn, these profiles define the boundaries of head and body movements well tolerated by the user without injury. At a functional level, these profiles are effectively representations of the three-dimension biomechanical properties of the user's head-and-neck. These profiles are different for different users and therefore are personalized for the user. In the present invention, information contained in these profiles therefore allows the sensor stage or the smart head-impact-monitoring system of the present invention to make decisions with a high degree of sensitivity and specificity as exemplified in many other devices of artificial intelligence (see below). Indeed, one of such important decision is whether the smart head-impact-monitoring system of the present invention has detected a head impact event that involves forces exceeding the boundaries of head and body movements well tolerated by the head-and-neck of the user.

The data may be sampled and generated from the first and second sensors 12, 14 at a given frequency, for example, 1 kiloHertz (kHz), resulting in one real-time measured sample every millisecond (1 ms). The processing element 22 may parse the data to identify a plurality of periods of motion, wherein each period of motion is the time during which the user's head, body, or both are moving. The processing element 22 may determine the point at which the real-time measured samples transition from being less than a motion threshold to greater than the motion threshold, wherein the motion threshold is a value of the measured data which indicates that motion of the user's head or body is occurring. The motion threshold may have a value in terms of velocity, acceleration, or the like. For the first period of motion, the processing element 22 may then indicate that the data received from the first and second sensors 12, 14 after the user starts moving is period of motion data. The indication may include tagging the subsequent data, placing the subsequent data in a specific location in the memory element 20, creating a virtual table or a database for the subsequent data, or the like. The period of motion data may include a stream of real-time measured samples, indicated in FIG. 6 as S1(n), where n may be 0, 1, 2, and so on. In some embodiments, each real-time measured sample may also include a time stamp indicating the time (of day) when the data value was measured. Thus, in an exemplary embodiment, the period of motion data may include or represent the measured value of the acceleration of the user's head or body in the first millisecond, the second millisecond, the third millisecond, and so forth after motion first started. The processing element 22 may continue indicating or marking the data from the first and second sensors 12, 14 as period of motion data until the value of any of the real-time measured samples falls below the motion threshold—indicating that the period of motion has ended.

Alternatively, the identification of the beginning of a period of motion may involve more than one real-time measured sample. This alternative refinement effectively distributes the burden, over several real-time measured samples rather than on single real-time measured sample, of identifying the beginning of a period of motion. For example, if two or three real-time measured samples are used to identify the beginning of a period of motion, the certainly of that identification will be many times better than if only one real-time measured sample is used.

Figure 6:
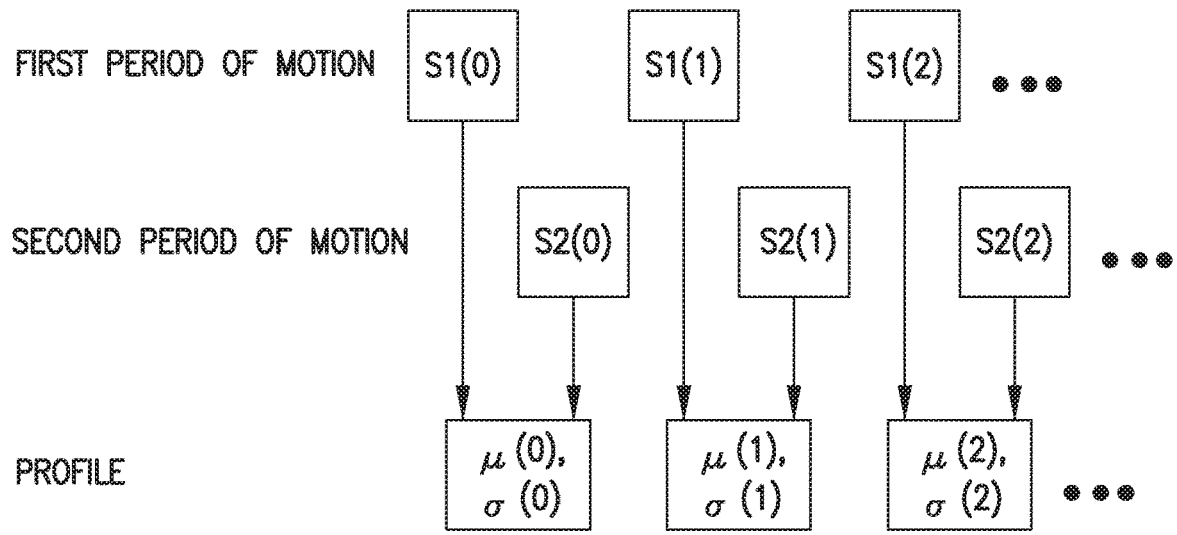
FIG. 6 is a block flow diagram depicting at least a portion of the creation of a profile for use with the device of FIG. 1.

Afterward, the processing element 22 may parse the data from the first and second sensors 12, 14 until it determines that the next period of motion, indicated in FIG. 6 as S2(n), has begun. Then, in an ongoing and real-time process, for each subsequent period of motion, the processing element 22 may determine the mean $\mu$, or average, of the first real-time measured sample of the current period of motion with the first real-time measured sample of all of the previous periods of motion. For example, using the real-time measured samples from just two periods of motion as shown in FIG. 6, the processing element 22 may calculate $\mu(0)$ as the mean of S1(0) and S2(0). The processing element 22 may also calculate other statistical data, such as the standard deviation (SD) or the standard error of the mean (SEM), etc. For example, using the real-time measured samples from just a few periods of motion as shown in FIG. 6, the processing element 22 may calculate $\sigma(0)$ as the standard deviation of S1(0), S2(0), etc. Furthermore, the processing element 22 may perform similar calculations of mean and standard deviation for the second and third and all of the subsequent real-time measured samples of the current period of motion. The statistical calculations of the mean, SD, SEM, and so forth for each sequential real-time measured sample may become a part of the contents of each cell of the profile. Thus, the first cell of the profile may include $\mu(0)$, $\sigma(0)$, and possible other statistical data. The second cell may include at least $\mu(1)$ and $\sigma(1)$. The other cells may follow suit.

The description of the present invention up to this point has made it clear that each unit of the sensor stage is to be dedicated or restricted to a single user. A direct consequence of this restriction is that the data acquired in this fashion by the processing element 22 is personalized or individualized to the said single user.

In some embodiments, however, each real-time measured sample may also include an identifier stamp indicating the identity of the user when the data value was measured. In some embodiments, each real-time measured sample may also include a more detailed stamp indicating the user's age, gender, body weight, height, body mass index, neck girth, head circumference, etc., when the data value was measured. The inclusion of time stamp, identifier stamp, more detailed stamp, as well as additional stamps may allow a single sensor stage in the present invention to be shared by multiple users. For example, a high school football coach may need to re-assign a given sensor stage to a different player in different seasons as some players may graduate and other new players join the team. In such shared usage, as long as the real-time measured data sample is properly tagged or stamped, a single sensor stage may keep track of the head and body movement of multiple users without losing the appeal that the sensor stage can still yield data that is individualized or personalized to individual users.

We now summarize the description up to this point, which covers a major working principle and the objective of the present invention—the device 10 is able to offer individualized protection custom-fit to the user. This objective may be accomplished by dedicate one device 10 to a single user. Or the objective may be accomplished at the level of processing element 22 as long as user identification stamp, time stamp, and other stamps are used to keep track of the data from sensor 12 and sensor 14.

Values of movement parameters of the head of the user (velocities, accelerations, etc.) may be analyzed statistically as the mean±SD. The entire profile, including the raw data as well as the results of statistical analysis, may be transmitted to a memory storage via a central server or via a cloud memory storage. The values of mean and SD for the normal movements of the user will be utilized to determine values for the dynamic concussion threshold.

In the present invention, the movement parameters of the head of the user (velocities, accelerations, etc.) may involve an organization. For example, before the statistical analysis, movement parameters (velocities, accelerations, etc.) may be broken down or decomposed into components about the pitch, roll, and yaw axes. In this way, those movement parameters (velocities, accelerations, etc.) on head movements may be organized into pitch, roll, yaw files.

The method of organization for the head movement data into pitch, roll, yaw files is based on recent findings in the inventor's laboratory. These findings are derived from results of analyzing head movements in video analysis of boxing matches associated with knockouts and control head movements that were not associated with knockouts. We clarify that the methodology of obtaining data on head accelerations from video analysis has been well established for more than a decade. The resultant data on head movement such as angular velocities, angular accelerations are comparable with those obtained with MEMS sensors. In our video analysis, we compared head angular velocities in KO (knockout or concussion) head hits and those in NKO (no knockout or asymptomatic) head hits. Head angular velocities in KO head hits were consistently higher than those in NKO head hits regardless of the observed head rotations being around pitch, roll, or yaw axis of rotation—the KO-NKO contrast being 1200±202 vs. 538±81°/s, 502±59 vs. 217±36°/s, and 744±64 vs. 569±32°/s, for pitch, roll, and yaw, respectively. All these differences were significant with p-values being $7 \times 10^{-3}$, $1.5 \times 10^{-3}$, and $1.4 \times 10^{-2}$ for pitch, roll and yaw NKO-KO comparisons, respectively. In summary, by examining the head angular velocities in pitch, roll, and yaw axes, it is possible to predict or distinguish between a KO hit and an NKO hit with ~99% accuracy, or at the p=0.01 level.

Among head hits in the pitch, roll, and yaw axes, KOs with head rotations around the roll axis occurred at lower levels of head angular velocities than KOs with head rotations around the pitch or yaw axis. It is as if the human head-and-neck is more vulnerable to concussive injuries or knockouts when the hits are in the roll axis. Indeed, the average head angular velocities in KOs with head rotations around the roll axis was 502±59°/s, only slightly lower (but not statistically significant) than the average head angular velocities in NKO hits with head rotations around the pitch and yaw axis (538±81°/s and 569±32°/s, respectively). It is clear, therefore, had one not noted the possible fact that the human head-and-neck is consistently (that is, in most persons) more vulnerable to concussive injuries in one axis than another, one might say that analysis of head velocities lacks the requite sensitivity and specificity for predicting concussions. Therefore, it is not sufficient to note that concussive thresholds are different from person to person (e.g. from a child to adult), one must additionally note that concussive thresholds are different, within a given person, dependent upon whether the head hits are in the pitch, row, or the yaw axis.

From these findings, the inventor recognizes that the concussion threshold of the human head-and-neck is significantly different in each of the pitch, roll, and yaw axis. For example, it is the inventor's views that the threshold for concussion is much higher for impact-induced head movements in the pitch axis than the yaw axis. From this example, therefore, potential concussive consequences of a head impact at a certain magnitude (in G units) cannot be accurately ascertained without considering whether it is in the pitch axis or the yaw axis. By contrast, organizing the impact force data or the head movement data into pitch, roll, and yaw axes is expected to significantly increase the accuracy of predicting the concussive outcome from such impact force data or the head movement data.

The inventor has carried out computational simulation in his laboratory to examine the utility of breaking down the impact force into pitch, roll, and yaw components in concussion prediction. We produced hypothetical cases in which the force levels in G units required for concussive injuries in each of the pitch, roll, and yaw axes clearly do not overlap with the force levels not causing concussive injuries. In these cases, therefore, examination of an impact event while paying attention to the magnitude of the force in each of the pitch, roll, and yaw cases separately resulted in 100% accuracy in prediction of concussions. We then mixed the impact event in the various axes together, invariably, the accuracy of predicting concussive injuries deteriorated, most of the time toward chance levels (e.g. between 50% to 60%). We mentioned earlier that the average head angular velocities in KOs with head rotations around the roll axis was not statistically different form the average head angular velocities in NKO hits in the pitch and yaw axes.

Furthermore, and according to the general principle of the Principal Component Analysis, potential concussive consequences of a head impact at a certain magnitude (in G units) cannot be accurately ascertained even if the directionality of the impact was taken into consideration but by another mutually orthogonal set of axes but not specifically using the framework of pitch, roll and yaw. The inventor recognizes that it is likely that the framework of pitch, roll, and yaw axes is not only the natural or biological framework to represent the biomechanical degree of freedom of movement for the human head-and-neck, but also the set of Eigenvectors for concussive analysis of the three-dimensional head movements.

A method of data organization based on the pitch, roll, and yaw framework should be beneficial, if not critical, to the goal of setting thresholds for concussive injuries. This view is supported, albeit indirectly, by a 2017 review article on the use and effectiveness of head-impact-measurement devices [O'Connor et al, Journal of Athletic Training, 52 (3) 206-227, doi 10.4085/1062-6050.52.2.05]. The authors concluded that, " . . . (such head-impact-measurement devices) did not have the requisite sensitivity to concussion. . . . head-impact-monitoring systems have limited clinical utility due to error rates, designs, and low specificity in predicting concussive injury." Coincidentally, the pitch, roll, and yaw analysis performed by the processing element 22 in the present invention was not used in the head-impact-measurement devices covered by the 2017 review article.

Those movement parameters of the body of the user (velocities, accelerations, etc.) may be organized into similarly mutually orthogonal directional files. A system similar to the pitch, roll, yaw axes for describing head movements should be appropriate as the body and the head are joined via a single, albeit, complex joint which constitutes the head-and-neck.

For both data on movement parameters of the head and the body of the user, one-tailed independent Student's t-tests or Mann-Whitney rank sum tests or the like may be used to test differences between data on movement parameters that can lead to concussive head injuries and data on movement parameters that does not lead to concussive head injuries.

We now summarize the description up to this point, which covers a major working principle of the present invention—to quickly make an accurate assessment of the injurious potential of a given head impact. The processing element 22 of the sensor stage accomplishes this task by separating forces or accelerations into pitch, roll, and yaw components. The framework of the pitch, roll, and yaw axes is associated with the biological degrees of movement freedom of the human head-and-neck (rather than any other arbitrary set of orthogonal coordinates X, Y, and Z). Because the thresholds of concussive injury are different dependent upon the directionality of the external impact force (pitch, roll, and yaw), the pitch-roll-yaw analysis of the present invention allows the sensor stage of the present invention to make the most accurate predictions of the injurious potential for a head impact event.

The device 10 may operate initially in a calibration mode and may later be switched from the calibration mode to a normal mode after a certain number, such as 1,000 or the like, of periods of motion have been analyzed or after a certain period of time has elapsed, such as one or two months. The mode of the device 10 may be switched from calibration to normal by an administrator or manufacturer via a manual operation of by sending a wireless signal to the communication element 18 when it is deemed that normal, voluntary, non-injurious, and non-concussion-inducing motion has been properly captured in the profile. Both the number of periods of motion and the period of time elapsed, which lead to the switch from the calibration mode to a normal mode, serve to indicate that the numerical attributes of the profile are statistically relevant. In other words, the mode is switched when it is deemed that the memory element 20 has a series of profiles that offer statistically relevant description of the user's head and body movements that are non-injurious. The profile may include a time-sequence ordered set of mean values, standard deviations, and other statistical values for parameters such as position, orientation, velocity, and acceleration for the head and the body. The data may be further organized in pitch, roll, and yaw axes, or the like.

Alternatively, the switch from the calibration mode to a normal mode for the device 10 may be done automatically as part of the machine learning capability of the sensor stage or the smart head-impact-monitoring system of the present invention. The processing element 22 continuously monitors and compares the various numerical attributes of the various profiles (e.g. values of mean and standard deviation) stored in the memory element 20. Initially or shortly after a new user begins to use our device, data on movement parameters of the head or the body of the user (velocities, accelerations, etc.) will generate values of mean and standard deviation based on just a small or limited data sample (e.g. from a data sample less than ten head movements or the like). When the size of the data sample is small, the resultant description of the movement profile is often not statistically valid. A sure sign of a profile on movement is not statistically valid is that the mean and standard deviation of that movement parameter profile will change significantly as more data on that movement parameter is added to the sample. Thus, as long as significant differences are detected in the various numerical attributes of the various movement parameters (e.g. comparing values of mean and standard deviation in Student's t-test, or the like) of the various profiles with use or with time, the calibration mode will continue. When the user has tried our device for a period of time and usage that is sufficiently long and extensive, and significant differences are no longer detected in values of mean and standard deviations of the various numerical attributes of the various movement parameters (e.g. position, orientation, velocity, acceleration, etc.) in the various profiles describing the normal, non-injurious head movements of the user, the calibration mode can end and the switch from the calibration mode to a normal mode can be made automatically by the sensor stage or the smart head-impact-monitoring system of the present invention.

The sensor stage or the smart head-impact monitoring system of the present invention is therefore designed to first machine-learn the normal, non-injurious movement profiles of the user's head and body. The user should tolerate his own normal, non-injurious movement about the head and body without concussive injuries. We next define a time-varying dynamic concussive threshold (DCT) in the present invention, based on the normal, non-injurious movement profiles of the user's head and body of the user. Since the data on movement parameters in normal, non-injurious movement about the head and body is likely to be different from different users, approaching the dynamic concussive threshold from the user's normal, non-injurious movement profile therefore results into an individualized definition of concussive threshold that custom-fit the user.

The term "dynamic" in DCT refers to the fact that the data on each movement parameter (e.g., position, orientation, velocity, acceleration, etc.) in the various movement profiles comprises time series of data points (e.g. 1 ms after movement initiation, 2 ms after movement initiation, and so on). Given that the parameters (e.g., position, orientation, velocity, acceleration, etc.) vary over time, so too will the DCT. A second reason for using the term "dynamic" in DCT is because the influence of the dynamic neck stiffness on concussive thresholds. Given that the neck stiffness varies with time, so too will the DCT. Once the sensor stage of the present invention is switched from a calibration mode to normal function mode, the processing element 22 analyzes each newly encountered head and body movement not only in the dimension of movement parameter (such as data from measurements of position or distance, orientation, velocity, and acceleration) but also in the dimension of time in order to detect data points that have exceeded the DCT.

Because of the multiple-dimension quality of the DCT, there generally will be a large number of data points (for example, >10) available for making the decision whether the DCT has been exceeded for a certain newly encountered head movement event. The large number of data points ensures that such a decision can generally be made more accurately within 5-7 ms of the movement initiation, long before the impact force has time to build up to an extent that may cause concussive injuries. The implication is that, if a countermeasure to dissipate the impact force/energy can be launched as soon as a decision is made, and this decision is highly accurate, the countermeasure should be quite effective in the prevention of concussive injuries.

Once a statistically relevant or invariant movement profile is created for the user, the device 10 may be configured or programmed to operate in the normal mode during which the user is engaging in activity that may involve impacts which could potentially cause a concussion. It is generally accepted that a concussion may occur when acceleration, as an exemplary parameter, of the head is greater than a concussion threshold value. In the present invention, the operation of the processing element 22 does not involve a single, fixed, and one-size-fits-all threshold. Instead, the operation of the processing element 22 is based on a dynamic concussion threshold (DCT), which is unique to each individual user. Therefore, value or values for DCT in units of G (gravity) may vary from user to user and is individualized or personalized.

The individualized or personalized feature of the present invention is consistent with the fact that the realistic concussion threshold may vary from user to user. For a given user, the DCT may also be unique for head rotations about each of the pitch, roll, and yaw axes. The DCT may also be different for different dynamic neck stiffness (DNS). The processing element 22 may therefore also set a different DCT for the same user dependent upon the directionality of the impact (e.g. in head rotations about pitch, roll, or yaw axes) as well as the DNS (see below).

We now summarize the description up to this point, which covers a major working principle of the present invention—to define and measure an individualized or personalized concussion threshold. The processing element 22 accomplishes this task by defining value or values for DCT relative to the user's mean, or average, levels of acceleration during normal activity in the present invention. Here the term "normal activity" is defined as those head or body movements that are normal, voluntary, non- injurious, and non-concussion-inducing. In other words, we (1) monitor head accelerations of the user in pitch, roll, and yaw axes in real time, (2) machine-learn the normal, non-injurious head movement parameters (e.g. accelerations, velocities, etc.) of the user, (3) use these parameters to define the boundaries between non-injurious and potentially injurious head movements, (4) use these boundaries to set personalized injury thresholds by determining when the head movement parameters of an impact are outside the normal and non-injurious range and may cause injury. In addition, the determination of DCT should take into account average levels of variation, or standard deviation, of acceleration during normal activity. For example, the processing element 22 may determine the dynamic concussion threshold value to be equal to the mean value of acceleration plus the standard deviation multiplied by a sensitivity factor, the value of which may be determined with considerations on the neck stiffness index. The value or values of DCT may therefore further vary with a neck stiffness index (see the description on the sensitivity factor below).

Since there is a mean and a standard deviation for each sequential value of velocity, acceleration, etc. in the profile that characterizes the user's normal, non-injurious movement patterns of the head and the body, which is well tolerated by the user without concerns on concussive head injuries, a dynamic concussion threshold can be statistically derived for each sequential value at each level of the sensitivity factor. For example, if the sensitivity factor is equal to one, then, the DCT is defined as those head movements with head velocity or acceleration that are equal to or more than the mean value of his normal head movements plus one standard deviation. Statistically, any head movement with biomechanical parameters (e.g. head velocities, accelerations, etc.) exceeding the mean value of his normal movement profile by one standard deviation has a probability of 15.9% as being part of the user's normal head movement. Alternatively, the processing element 22 may conclude that there is an 84.1% probability that such head movement may be caused by potentially injurious external forces (as opposed to initiated by the user). For another example, if the sensitivity factor is equal to two, then, the DCT is defined as those head movements with head velocity or acceleration that are equal to or more than the mean value of his normal head movements plus two standard deviation. Statistically, any head movement with biomechanical parameters (e.g. head velocities, accelerations, etc.) exceeding the mean value of his normal movement profile by two standard deviation has a probability of 2.3% as being part of the user's normal head movement. Alternatively, the processing element 22 may conclude that there is a 97.7% probability that such head movement may be caused by potentially injurious external forces (as opposed to initiated by the user). For a third example, if the sensitivity factor is equal to three, then, the DCT is defined as those head movements with head velocity or acceleration that are equal to or more than the mean value of his normal head movements plus three standard deviation. Again, statistically, any head movement with biomechanical parameters (e.g. head velocities, accelerations, etc.) exceeding the mean value of his normal movement profile by three standard deviation has a probability of 0.1% as being part of the user's normal head movement. Alternatively, the processing element 22 may conclude that there is a 99.9% probability that such head movement may be caused by potentially injurious external forces (as opposed to initiated by the user). The numbers 15.9, 2.3, 0.1% are taken directly from a statistical table on one-tailed normal distribution.

In some embodiments, therefore, the processing element 22 may use a formula to calculate the dynamic concussion threshold for each sequential value in the profile incorporating the sensitivity factor. For example, the formula may include a sensitivity factor (SF) in the following fashion: $DCT(n)=\mu(n)+SF \times \sigma(n)$. Values of the sensitivity factor may be determined with consideration of the neck stiffness index. Generally, a smaller SF value may be used in a user with a neck stiffness index associated with a more flexible or less stiff neck. Also generally, smaller values of the SF render the device 10 more sensitive or restrictive, i.e., the locking signal is asserted at lower values of acceleration. Larger values of the SF render the device 10 less sensitive or less restrictive, i.e., the locking signal is asserted at higher values of acceleration. Exemplary values of the SF may range from less than one to more than one. Smaller values of SF under one may be particularly suitable for protection against sub-concussive impact events, an action that may be pertinent for children and adolescents whose head-and-neck is still under development. In some situations, the SF may be set, such as by entering values on an electronic device (computer, smart phone, etc.) connected to the device 10, manually by an administrator or a user. The SF may be set to a value of less than 1 in order to increase the sensitivity of the device 10. The SF may be set to a value greater than 1 to decrease the sensitivity of the device 10.

Additionally, or alternatively, the SF may be set automatically by the processing element 22 based on, or varying according to, a dynamic neck stiffness index (DNSI). Concussions are consequences of inopportune and inappropriate interactions between an impact force and the head. The encounter is inopportune as it often occurs when the impact force catches the head-and-neck in a moment of little or no stiffness. It is the view of the inventor, as well as many other experts in the field, that information or data on neck stiffness is important, if not critical, to the accurate assessment of the potential of impact-induced head movements in concussive injuries.

Before describing our method of obtaining data or information on neck stiffness, we clarify first that the measurement of neck stiffness described in the present invention is different from how stiffness is defined and measured in a conventional sense. Wikipedia defines stiffness as a relationship between stress (force per unit area) and strain (proportional deformation). In this regard, Young's modulus and other forms of definitions and methods of measurement for stiffness in material science are quite consistent—they are always about stress and strain. The traditional methods for the measurement of stiffness, including neck stiffness, is time consuming and cumbersome. For practical reasons, therefore, the method to get at the neck stiffness in the present invention does not directly measures stress or strain. The results of the measurement for neck stiffness described in the present invention, however, should correlate in principal rather well with the traditional definition and measurement of neck stiffness. For this reason, we will be using the term stiffness index when we refer to the results on neck stiffness from the measurement of neck stiffness described in the present invention. For example, DNSI refers to dynamic neck stiffness index. We now define how DNSI is measured in the present invention. We begin by describing a method of obtaining data or information on neck stiffness with the first sensor 12 and the second sensor 14.

The head is connected to the body via the neck, which functions effectively as a single, albeit complex joint involving seven cervical vertebrae. Although each of the vertebrae has a limited range of motion with respect to its adjacent neighbor, both the head and the body move whenever a force acts on the head or the body of the user. The relationship between the biomechanical parameters of head movement and those of body movement is therefore determined by the characteristics of the neck, sometimes also referred to as the head-and-neck in the literature. In the present invention, the processing element 22 may further determine or calculate a neck stiffness index as a ratio of the data, such as acceleration, from the second sensor 14 to the data, such as acceleration, from the first sensor 12. Or the data may include measurements of position or distance, orientation, velocity, and acceleration, and so on. One way to process or express such data on accelerations is to organize the data from the first sensor 12 and the second sensor 14 into components about the pitch, roll, and yaw axes in accordance with the natural or biological degree of freedom of the human head-and-neck. If the user's neck is perfectly stiff or nearly as stiff as a steel column the size of the user's neck, then the output of the first sensor 12 and the second sensor 14 may be generally close in all three of the axes—pitch, roll, and yaw. Indeed, if the external force acts on the center of mass of the head-and-neck construct with a perfectly stiff neck, the output of the first sensor 12 and the second sensor 14 may be identical, generating a neck stiffness index of unity or one (about each of the pitch, roll, and yaw axes). Generally, if a force acts on the head with a neck less stiff than perfect may result into a condition in which the first sensor 12 (affixed to the head) may register a larger acceleration than the second sensor 14 (affixed to the body), generating a neck stiffness index smaller than 1. This observation may be made with other data including measurements of position or distance, orientation, velocity, and acceleration. This observation may also be made when the impact force is delivered to the head or when the impact force is delivered to the body. For example, and under certain conditions, preliminary results from the inventor's laboratory (not published yet) indicated that the neck stiffness index of a male college student may reach a value of 0.6 while the neck stiffness index of a female college student may reach a value of 0.4 for head movements about the pitch axis.

The neck stiffness index is therefore a vector entity with pitch, roll, and yaw components. The neck stiffness index is also a dynamic parameter whose value can change with time (for example, millisecond by millisecond) and each single head movement. For example, the neck stiffness is typically rendered to zero or very close to zero (by volitional neuromuscular action of the user) prior to making a voluntary head movement, as nodding in saying yes, shaking one's head while saying no, or as a quarterback scanning the field for open receivers. It may also be a function of the position, velocity, and acceleration of head movement and body movement. In the present invention with the two-sensor system, data on DNSI can be streaming into the processing element at the sampling rate of sensor 12 and sensor 14, or at 1 kHz. DNSI may be stored in the memory element 20 and is unique for each user. Ultimately, information on the DNSI on a given user may also be transmitted to a memory storage via a central server or via a cloud memory storage. The utility of DNSI can include, but is not limited to, an application in concussive as well as sub-concussive protection rendered by the processing element 22 via a sensitivity factor.

Under certain circumstances, such as when the user is sitting, standing, or otherwise resting quietly without gross head and body movements, the output from sensor 12 and sensor 14 may be low, e.g. between 1 G and 3 G. If gravity or 1 G is subtracted from the output of sensors 12 and 14, and we arbitrarily set the noise level to be 0.1 G, the ratio between the output of sensor 12 and 14 can be between the 20 (e.g. 2/0.1) and 0.05 (0.1/2). First, it is clear that values of DNSI should not be more than unity. It is further clear that the neck stiffness does not vary so much such as between 0.05 and 20 when a person is resting quietly. It is therefore prudent, and also easy, for us to recognize this. For example, whenever the ratio of the output from sensor 12 and the output from sensor 14 is therefore a small number divided by another small number, and the resultant ratio being possibly quite noisy, the processing element 22 may be programmed to recognize such circumstances, acknowledges that the dynamic neck stiffness (DNS) is low, and assigns a low value for DNSI.

It is the view of the inventor, as well as many other experts in the field, that information or data on DNS is important, if not critical, to the accurate assessment of the potential of impact-induced head movements in concussive injuries. This view is supported, intuitively albeit indirectly, by a 2017 review article on the use and effectiveness of head-impact-measurement devices [O'Connor et al, Journal of Athletic Training, 52 (3) 206-227, doi 10.4085/1062-6050.52.2.05]. The authors concluded that, " . . . (such head-impact-measurement devices) did not have the requisite sensitivity to concussion. . . . head-impact-monitoring systems have limited clinical utility due to error rates, designs, and low specificity in predicting concussive injury." Coincidentally, dynamic neck stiffness such as one indicated by the dynamic neck stiffness index derived by the processing element 22 of the sensor stage in the present invention was not used in the head-impact-measurement devices covered by the 2017 review article.

We now summarize the description up to this point, which covers a major working principle of the present invention—to define and measure the dynamic neck stiffness of the user. The processing element 22 of the sensor stage accomplishes this task by deploying two (or more than two) sensors in order to measure simultaneously forces or accelerations of the head and the body. This arrangement allows the sensor stage of the present invention to obtain data on dynamic neck stiffness such as DNSI. Many concussions occur as the impact force catches the head-and-neck in a state of low neck stiffness. Data or information on DNS such as the data DNSI in the present invention is therefore important and will be used by processing element 22 to determine the dynamic concussive threshold (see below).

The processing element 22 receives measured samples from the first sensor 12 and the second sensor 14. The processing element 22 may compute, calculate, or determine the DNSI as the quotient of the measured samples from the second sensor 14, which is typically coupled to the body component 26 or body apparatus, and the measured samples from the first sensor 12, which is typically coupled to the head component 24 or head apparatus. Thus, the DNSI may be the measured samples from the body, $SB(n)$, divided by the measured samples from the head, $SH(n)$, or $SB(n)/SH(n)$. The DNS and the DNSI change with time, assuming lower values as the user turns his head and assuming higher values when the user is prepared to exert force or prepared to take force in the head-and-neck region.

The processing element 22 may compute, calculate, or determine the SF according to the equation: $SF=K \times DNSI$ where K is a coefficient with a value of 1 or 2. The sensor stage or the smart head-impact-monitoring system of the present invention monitors DNS continuously and will set the sensitivity factor SF according to the DNSI, in real time, in order to provide the maximal protection for the user. In this way, the dynamic concussion threshold not only is an individualized parameter, custom-fit to the user (because the dynamic concussion threshold is derived from the normal, non-injurious head movements of the user), but also changes with time according to the user's dynamic neck stiffness. Anticipating that concussive head injuries are more likely to occur when the neck stiffness is low, this feature is designed to offer more protection (in conjunction with the activation of the linkage elements) especially when the dynamic neck stiffness of the user is low. In certain embodiments, the processing element may use a logic operation to determine SF such as by the formula $SF=$ the smaller value of $K \times DNSI$, where K is a small constant with a value of 1 or 2 and 0.5.

Figure 7:
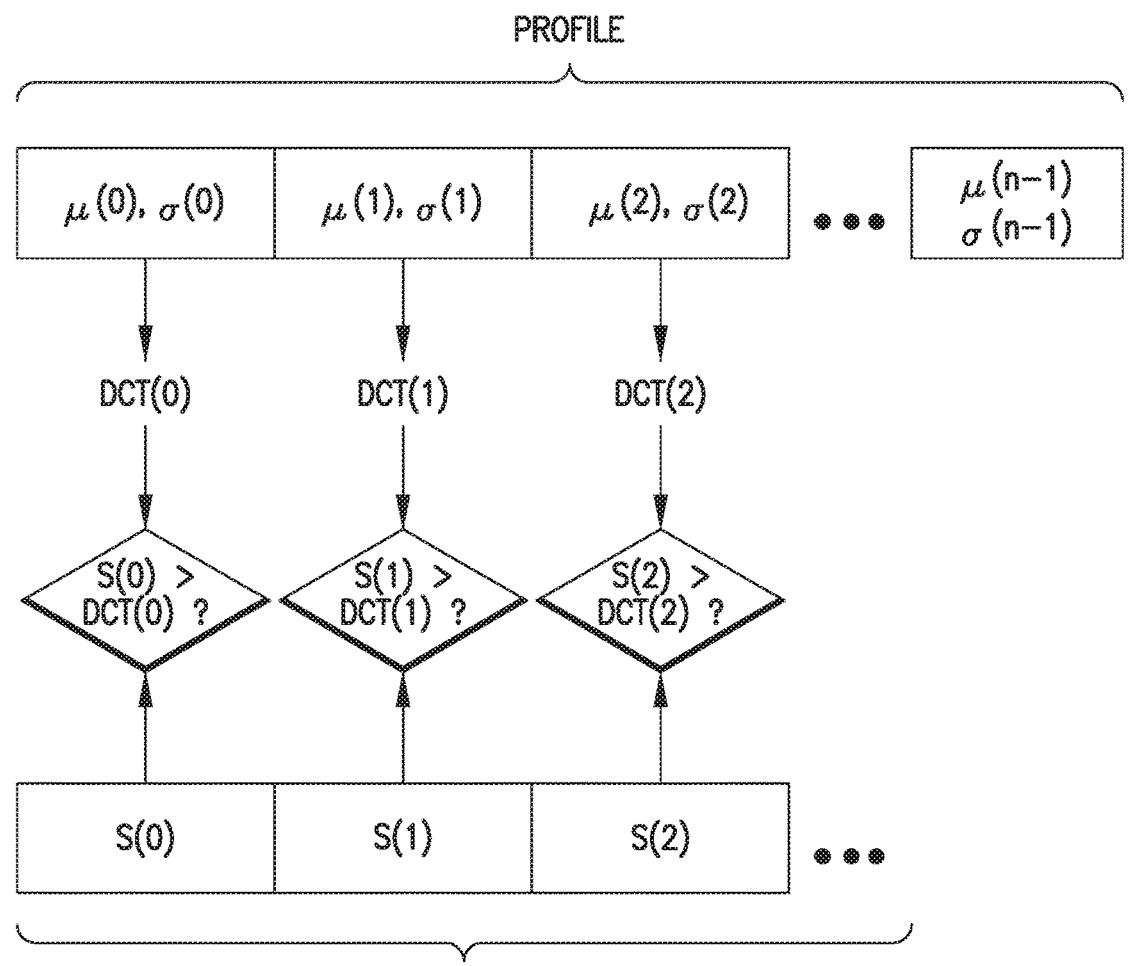
FIG. 7 is a block flow diagram depicting at least a portion of the comparison of real-time measured samples with dynamic concussion thresholds for use with the device of FIG. 1.

The processing element 22 may parse real-time data that is supplied by the first and second sensors 12, 14. Once the start of a period of motion is detected, the processing element 22 may compare the real-time measured samples with the dynamic concussion threshold, as depicted in FIG. 7. The processing element 22 may retrieve the mean $\mu(0)$ and the standard deviation $\sigma(0)$ for the first sequential value in the profile and compute the first value of the dynamic concussion threshold $DCT(0)$, which is then compared to the first real-time measured sample $S(0)$, depicted as $S(0)>DCT$ (0)? The processing element 22 may further compute a second value of the dynamic concussion threshold that is compared with the second real-time measured sample. The processing element 22 may continue computing values of the dynamic concussion threshold and comparing them with the corresponding real-time measured samples for all of the real-time measured samples of the current period of motion.

We now summarize the description up to this point, which covers a major working principle of the present invention—the dynamic concussion threshold (DCT) in the present invention is not a single, one-size-fits-all, quantity but closely coupled to DNSI. Although it is largely based on an individualized profile of the user's own normal, voluntary, non-injurious, and non-concussion-inducing head and body movements, the setting of DCT may involve a great deal of flexibility while taking DNSI into consideration. For one example, because the DCT is based on the profile of the user's own normal, non-injurious, and non-concussion-inducing head and body movements, DCT is generally at a lower G force value than a force value that is known to cause or likely to cause a concussion. For another example, the sensitivity factor SF can be set by an administrator for a child who may desire extra protection. In addition, the sensitivity factor (SF), determined together with DNSI can offer the opportunity for adjusting the level of protection by adjusting DCT, in real time and automatically. By making the generation of a locking signal at a lower acceleration while DNS is low, the operation of the processing element 22 becomes more sensitive. Because the actions of the locking signal is brief (generally less than 100-200 ms), such actions are unlikely to interfere significantly with voluntary head-and-neck movements. The benefit will be significant, however, as we dial back the sensitivity factor (SF) to smaller values to address the protection of the user against sub-concussive impact events (see below).

From published accelerometer data obtained from football players, it is possible that the acceleration possibly leading to a concussion reaches its peak value between 10 ms and 15 ms after impact. Also from published accelerometer data obtained from football players, it is possible that the acceleration possibly leading to a concussion lasts no longer than 100 or 200 ms. From results of high-speed video analysis of boxing matches in the inventor's laboratory, it is possible that a concussion process may start or take place between 30-50 ms after an impact of the knockout type. These data dictates that a preventive countermeasure to reduce the risk of concussion must be launched quickly, preferably within single digit of ms and not longer than 30 ms when a concussion may take place. In addition, the duration of the countermeasure needs not to be longer than 100 or 200 ms.

The sensitivity of modern accelerometers is generally of the order of a fraction of 1 G. The peak or maximal force or acceleration involved in a concussion is generally of the order of 30 G or more. The acceleration or force increases to reach a peak or maximum value in a monotonic fashion with time, typically between 10 ms and 15 ms after impact and, most of the time, within 20 ms after the impact. From such data or information on how impact force/energy builds up with time, it may be possible to detect the trajectory of acceleration that might cause a concussion within a short time period, before the acceleration reaches its peak value—for example, approximately 5 ms to approximately 7 ms after an impact when sensors 12 and 14 may register forces with magnitudes that generally do not cause brain injury or concussion, e.g. between 5-10 G, or less. Thus, the processing element 22 may start a counter or otherwise track the values of the real-time measured samples right after the identification of a period of motion (see FIG. 6) in order to determine the timing and the occurrence of a first real-time measured sample whose value exceeds the dynamic concussion threshold. If the processing element 22 determines that each value of the consecutive real-time measured samples for at least 5-7 ms worth of real-time measured samples exceeds the dynamic concussion threshold, then it is likely that a concussion may occur when the acceleration or the impact force builds up to its peak or maximal value unless countermeasures are taken. The value of 5-7 ms is selected to describe our invention as exemplary time periods because it was demonstrated in the inventor's laboratory (not published yet) that commercial grade accelerometers can be readily programmed to predict the peak magnitudes of impact forces (which generally occur at 10-20 ms after impact) from data in the first 5-7 ms of impact with a success rate generally better than 99%. This exercise was carried out in the inventor's laboratory with data from a single "channel" of information as defined in Shannon's information theory. Recall that the parameter DCT is a function of time and is also a vector with pitch, roll, and yaw components. There will be, therefore, effectively many channels of information available to the sensor stage of the present invention. More channels of information all but ensure that a decision on whether an impact may be injurious can be made with high sensitivity and specificity within 5-7 ms of the impact. It is expected that at, for example, 5-7 ms after an impact, both the real-time measured acceleration data samples and the DCT (also within 5-7 ms of the impact) will not exceed 5-10 G, values that are not sufficient to cause concussive injuries. Consequently, the processing element 22 may generate the locking signal while the sensors 12 and 14 are still experiencing and reporting accelerations that are significantly under values that could cause brain injury or a concussion. In this way, the locking signal in the present invention is therefore generated ahead of or before a concussion could take place. The locking signal may be embodied by an electrical voltage, an electrical current, or another electrical parameter, or a binary data stream, a binary code, or the like.

The locking signal may be generated, activated, or asserted for a range from approximately 100 ms to approximately 200 ms. Then, the locking signal is deactivated or de-asserted. Because the duration of the locking signal is between 100 to 200 ms, the accompanying rigidity of the linkage elements 16A and 16B may only impose minimal effect on the degree of freedom of head movements (an eye blink is generally between 300 to 400 ms). Thus the user's ability to engage in athletic activities such as during a game of American football or to engage in required tasks such as during training for an athlete or during combat for a soldier, etc. may only be affected minimally.

We now summarize the description up to this point, which covers a major working principle of the present invention—the onset and the duration of the locking signal issued by the processing element 22 as well as the onset and the duration of the rigidity of the linkage elements 16A and 16B are both fast and brief. It is sufficiently fast such that the linkage elements 16A and 16B are activated for the dissipation of impact force/energy before such force/energy can injure the brain. We do not wait for the peak acceleration or force to develop. By that time, it may be too late either because a concussion has already occurred or because there is not enough time to launch an effective countermeasure to stop or prevent the concussion from occurring. Instead, our strategy is to sample and analyze the data from sensor 12 and sensor 14 when the data is still in its initial rising phase. We aim to predict the peak value and issue a locking signal when the analysis of the data still in its initial rising phase indicates that the eventual peak acceleration or force will be injurious. The actions of linkage elements 16A and 16B are sufficiently brief such that the rigidity associated with the activation of linkage elements 16A and 16B does not impose significant interference to the degree of freedom in head movements.

The processing element 22 may be further configured or programmed to update the profile. When the device 10 is in the normal mode, the processing element 22 continues to identify periods of motion in order to determine whether real-time measured samples of acceleration, for example, may potentially lead to a concussion. At the same time the processing element 22 is comparing the real-time measured samples with the corresponding values of the profile, the processing element 22 may also incorporate the most recently measured real-time samples of acceleration, velocity, etc. into the averaged values of the corresponding profile as long as the most recently measured real-time samples of acceleration, velocity, etc. do not cause the processing element 22 to generate a locking signal. That is, the processing element 22 may incorporate into average the first measured acceleration value for the head of the current, real-time period of motion with the first value of the profile for the same parameter in order to arrive at a new average. The processing element 22 may also calculate a new standard deviation and other statistical values. In this way, the processing element 22 may continuously update the profile by calculating the mean, the standard deviation, and the like for each sequential real-time measured sample and corresponding profile value. Such changes in the profile describing normal, non-injurious head and body movement of the user may be the result of maturation and growth as in children and adolescents. Such changes may also be the result of a user gaining more experience and expertise in a particular sport as a result of training and practice.

In some embodiments, the processing element 22 may not perform these calculations if it determines that the real-time measured sample values are greater than the concussion threshold, because those real-time measured samples are likely indicative of abnormal motion, which should not be included in the profile describing the user's normal, voluntary, non-injurious, and non-concussion-inducing head and body movements.

The processing element 22 may replace the values in the profile with the newly calculated mean, standard deviation, and the like for each of the parameters in the profile. In this way, the processing element 22 adapts the profile together with the DCT to the changing behavior of the user over time. The history of such adaption or changes may also be stored in memory (see below). The ability of the sensor stage in the present invention to update its data on the profile of normal and non-injurious head and body movement of the user allows the present invention to offer protection that is not only custom-fit to the user but also "grow" with the user.

The processing element 22 may also be configured or programmed to communicate the real-time measured data to a central computer server or a cloud memory and computing mechanism. The processing element 22 may communicate the data to the communication element 18 which in turn, transmits the data wirelessly to the server. Alternatively, the data may be transferred from the first and second sensors 12, 14 to the communication element 18. The server may then execute a software application which receives the real-time measured data from a plurality of devices 10. The software application may perform additional statistical calculations, such as the average or mean, the standard deviation, and the like, on the data. Thus, the software application may create a general population profile. In certain instances, the software application may create population profiles that are age specific, gender specific, and the like. In some embodiments, the device 10 in conjunction with data from the central server or a cloud memory and computing mechanism may further use the age specific, gender specific population profile to identify user or users whose device 10 may be generating data that is sufficiently "out of the norm" to warrant subsequent scrutiny, including a service call in order to identify whether the underlying reason for being "out of the norm" concerns the performance of the equipment or concerns the performance of the user.

In some other embodiments, the device 10 may have the general population profile stored in the memory element 20 when the device 10 is manufactured, thereby eliminating the use of the calibration mode, because the profile would already be built in. The processing element 22 may also derive the profile for the individual user over time in the manner described above.

We now summarize the description up to this point, which covers the generation and maintenance of an adaptive DCT. In the present invention, the DCT allows protection that is not only custom-fit to the user but also "grow" adaptively with the user.

We now describe how the device 10 may operate having described the major features of the present invention, which include the pitch-roll-yaw analysis, the monitoring of DNS, the determination of a personalized DCT, the tracking of harmful, sub-concussive head impact events.

The device 10 may operate as follows. The user may wear the device 10, the body component 26, and the head component 24, as shown in FIGS. 1 and 2. The first sensor 12 may be coupled to the head component 24, and the second sensor 14 may be coupled to the body component 26. The first linkage element 16 may be coupled to the left side of the head component 24 and the upper left side of the body component 26. The second linkage element 16 may be coupled to the right side of the head component 24 and the upper right side of the body component 26. In addition, the communication element 18, the memory element 20, and the processing element 22 may be mounted on a printed circuit board, or similar substrate, that is typically sealed within a package. Furthermore, the package may be attached to the interior of the head component 24 or housed in a cavity of the body component 26.

In some embodiments, the user may initially operate the device 10 in the calibration mode in order to create head movement and body movement profiles individualized to the user. The profile is needed for the processing element 22 to determine what motion of the head and body is normal, voluntary, non-injurious, non-concussion-inducing and what motion of the head and body may lead to a concussion. While the device 10 is in the calibration mode, the processing element 22 does not generate the locking signal and the first and second linkage elements 16A, 16B may always remain flexible. In order to properly create the profile, the user may engage in normal "safe" activity. For example, if the user plays American football, then he may kick or punt the ball, run with the ball, throw and catch passes, etc., without being tackled or tackling in such a way as to produce concussive injuries to the user. The first and second sensors 12, 14 transmit data to the processing element 22 on a continuous, or near-continuous, basis. The processing element 22 analyzes the data to determine when the user is engaged in periods of motion. During each period of motion, the processing element 22 performs calculations to develop the profile, as indicated in FIG. 6. Once sufficient data is collected to create the profile, the mode of the device 10 can be switched from the calibration mode to the normal mode.

In other embodiments, the device 10 may include a general population profile when it is assembled. Thus, it is not necessary for the user to initially operate the device 10 is the calibration mode.

After the profile is created, or if the device 10 includes a general population profile, the device 10 may operate in the normal mode. The normal mode is for use when the user engages in activity, such as American football, wherein there is the potential for a concussion to occur or there is a need to render sub-concussive to the user. During the activity, the first and second linkage elements 16A, 16B are normally flexible, allowing a full range of motion between the head component 24 and the body component 26. The first and second sensors 12, 14 are continuously, or nearly continuously, transmitting measured data, or real-time measured samples, to the processing element 22. The processing element 22 analyzes the data to determine when the user is engaged in periods of motion. Once a period of motion begins, the processing element 22 may monitor the data, as indicated in FIG. 7, to detect the beginning of motion that may lead to a concussion. Specifically, the processing element 22 may analyze the movement data with reference to the pitch, roll, and yaw axes of the user and determine whether the real-time measured sample values exceed the dynamic concussion threshold for a time period of approximately 5-7 ms or more, but not longer than approximately 20-30 ms when a concussion may start or take place. If the processing element 22 detects this sequence of potentially injurious motion, then the processing element 22 may generate the locking signal, all the while monitoring DNS and take DNSI into consideration in setting DCT.

In addition, or instead, the processing element 22 may receive the measured samples from the sensors 12, 14, may compare the measured samples with the motion threshold, and may perform the following steps while the measured samples are greater than the motion threshold. The processing element 22 may calculate a plurality of dynamic concussion thresholds, with each dynamic concussion threshold being associated with one of a plurality of sequential, time-based array cells. Each array cell may include a mean and a standard deviation of historically-collected measured samples from the sensors 12, 14, such that each dynamic concussion threshold is calculated as a sum of the mean and the standard deviation multiplied by a sensitivity factor for the associated array cell. The processing element 22 may compare successive sequences of measured samples with successive sequences of dynamic concussion thresholds. The processing element 22 may also generate the locking signal when each measured sample of one of the sequences of measured samples is greater than the corresponding dynamic concussion threshold of a corresponding sequence of dynamic concussion thresholds.

Furthermore, each sequence of measured samples includes a plurality of sequentially-recorded measured samples, S(n), starting with a first measured sample and ending with a last measured sample and each successive sequence starts with a next measured sample after the first measured sample of the previous sequence and ends with a next measured sample after the last measured sample of the previous sequence. This creates a moving window of measured samples, wherein the window forms a sequence and each sequence includes the same number of measured samples. For example, if each sequence of measured samples includes ten samples, then a first sequence may include the measured samples: S(0), S(1), . . . , S(9). A second sequence may include the measured samples: S(1), S(2), . . . , S(10). A third sequence may include the measured samples: S(2), S(3), . . . , S(11). And so forth.

Each sequence of dynamic concussion thresholds includes a plurality of sequentially-calculated dynamic concussion thresholds, DCT(n), starting with a first dynamic concussion threshold and ending with a last dynamic concussion threshold and each successive sequence starts with a next dynamic concussion threshold after the first dynamic concussion threshold of the previous sequence and ends with a next dynamic concussion threshold after the last dynamic concussion threshold of the previous sequence. This creates a moving window of dynamic concussion thresholds, wherein the window forms a sequence and each sequence includes the same number of dynamic concussion thresholds. For example, if each sequence of dynamic concussion thresholds includes ten values, then a first sequence may include the values: DCT(0), DCT(1), . . . , DCT(9). A second sequence may include the values: DCT(1), DCT(2), . . . , DCT(10). A third sequence may include the values: DCT(2), DCT(3), . . . , DCT(11). And so forth.

When sequences of measured samples are compared to sequences of dynamic concussion thresholds, the first sequence of measured samples may be compared to the first sequence of dynamic concussion thresholds, wherein S(0) is compared to DCT(0), S(1) is compared to DCT(1), and so forth until S(9) is compared to DCT(9)—assuming each sequence includes ten samples or values. The second sequence of measured samples may be compared to the second sequence of dynamic concussion thresholds, wherein S(1) is compared to DCT(1), S(2) is compared to DCT(2), and so forth until S(10) is compared to DCT(10). The third sequence of measured samples may be compared to the third sequence of dynamic concussion thresholds, wherein S(2) is compared to DCT(2), S(3) is compared to DCT(3), and so forth until S(11) is compared to DCT(11). And so forth. When the measured samples are greater than the values of the dynamic concussion threshold for an entire sequence, then the processing element 22 may generate the locking signal.

In some embodiments, the processing element 22 may perform a variation of the algorithm to determine whether the user is experiencing potentially concussive motion. The processing element 22 may receive the stream of measured samples, S(n), from the first sensor 12 and the second sensor 14, wherein each measured sample may include a plurality of components. Exemplary components may include two motion values, such as velocity (V) and acceleration (A), from each of the three axes, e.g., pitch (P), roll (R), and yaw (Y), of each sensor 12, 14. Thus, the sensors 12, 14 generate, and the processing element 22 receives, twelve motion values in total—VP1, VR1, VY1, AP1, AR1, AY1, VP2, VR2, VY2, AP2, AR2, and AY2. Furthermore, the twelve motion values are generated and received once every sample time period. For example, if the sensors 12, 14 sample measured values at 1 kHz, then the twelve motion values are generated and received every 1 ms. In addition, the contents of the profile may reflect the makeup of the data generated by the sensors 12, 14. Therefore, each cell in the profile may include statistical values (mean, standard deviation, etc.) for each of the twelve motion values. In other words, each cell includes a mean and a standard deviation, at least, for VP1, a mean and a standard deviation for VR1, and so forth for the rest of the twelve motion values.

Once the processing element 22 has determined that motion (or a period of motion) has begun, it may start comparing measured samples to the dynamic concussion threshold, DCT(n). Since the DCT is calculated for each cell in the profile and the profile is based on the measured samples, the DCT may include a plurality of components as well. The DCT may be calculated for each of the twelve motion values for each cell. Hence, for each cell, there may be a DCT for VP1, a DCT for VR1, and so forth for the rest of the twelve motion values. The DCT for any one of the motion values (for any given cell, n, of the profile) may be calculated using the equation: $DCT(n)=\mu(n)+\sigma(n)$, or by the equation: $DCT(n)=\mu(n)+SF\times\sigma(n)$, where SF is the sensitivity factor, or by other equations. The first measured sample S(0) may be compared to the first DCT(0), wherein the measured sample S(0) and the DCT(0) may each include all of the components or only a portion thereof, such that each component of the measured sample S(0) is compared with the corresponding component of the DCT(0). The second measured sample S(1) may be compared to the second DCT(1) in a similar fashion. And, successive measured samples S(n) may be compared to successive DCT(n) similarly. The processing element 22 may include, or be in communication with, a counter. If a measured sample S(n) is greater than the corresponding DCT(n), then the processing element 22 may start the counter, such that the count=1. For each consecutive, sequential, or successive measured sample that is greater than the corresponding DCT, the processing element 22 may increment the counter, such that count=count+1. If a consecutive, sequential, or successive measured sample is not greater than the corresponding DCT, then the processing element 22 may reset the counter, such that the count=0. If the count is equal to a predetermined concussion threshold value, meaning that a predetermined number of consecutive, sequential, or successive measured samples are greater than the corresponding DCTs, then the processing element 22 may generate the locking signal.

In other embodiments, the processing element 22 may include, or be in communication with, a timer instead of, or in addition to, the counter. In a similar situation as above, the processing element 22 may be comparing successive measured samples S(n) to successive DCT(n). If a measured sample S(n) is greater than the corresponding DCT(n), then the processing element 22 may start the timer. The timer may have a resolution of milliseconds or microseconds. For each consecutive, sequential, or successive measured sample that is greater than the corresponding DCT, the timer may continue running. If a consecutive, sequential, or successive measured sample is not greater than the corresponding DCT, then the processing element 22 may stop the timer and reset it. If the time of the timer indicates that a predetermined concussion threshold time (for example, 15 ms) has elapsed, then the processing element 22 may generate the locking signal.

The locking signal may be received by the locking elements 38 of the first and second linkage elements 16A, 16B. In exemplary embodiments, each locking element 38 may include a solenoid with a movable core that can be extended into the bypass element 36 of each linkage element 16A, 16B. When the locking element 38 of each linkage element 16A, 16B receives the locking signal, the locking element 38 extends the core into the bypass element 36 of each linkage element 16A, 16B such that the flow of the fluid medium 46 is stopped—rendering each linkage element 16A, 16B rigid. As a result, the relative position of the head component 24 to the body component 26 is locked or frozen. In this locked or frozen state, the rigidity of the linkage element 16A and 16B provides an impedance-preferred pathway such that the energy of the impact to the head is preferentially dissipated through the body component 26 and the user's body, thereby preventing the energy of the impact from causing brain injury. The locking signal may be generated such that the locking element 38 is active and the linkage elements 16A, 16B are rigid for approximately 100 ms to approximately 200 ms. After that time period, the locking signal is no longer generated, the locking element 38 retracts its core from the bypass element 36, the fluid medium 46 may flow, and the linkage elements 16A, 16B are flexible again.

When an impact to the user occurs, particularly on the upper body, the first and second sensors 12, 14 may generate measured samples whose motion values (e.g., velocity, acceleration, etc.) correspond to a sudden increase over a short period of time. The processing element 22 may receive the measured samples and compare them with the DCT, as described above. If the processing element 22 determines that the measured samples meet the potential concussion threshold criteria (i.e., the measured samples exceed the DCT for a predetermined number of samples or a predetermined period of time), then the processing element 22 generates the locking signal and the linkage element 16A, 16B locks in a rigid state. For the device 10 of the current invention, these events, from impact to the user to locking of the linkage element 16A, 16B, occur in less than or equal to approximately 20 ms.

The sensitivity of the device 10 may be adjusted by varying the sensitivity factor which adjusts the value of the dynamic concussion threshold. The sensitivity factor is determined in a fashion that renders it to be low when the DNS is low and to be high when DNS is high. Generally, decreasing the sensitivity factor renders the device 10 more restrictive, while increasing the sensitivity factor makes the device 10 less restrictive. The sensitivity factor may be adjusted through a software interface, such as a mobile electronic device (smartphone, tablet, or notebook) app. The value of the sensitivity factor may then be transmitted wirelessly from the mobile electronic device to the communication element 18, which in turn transfers the value to the processing element 22 or stores the value in the memory element 20.

While the device 10 is in the normal mode, the profile may be updated while the user is engaged in activity that does not potentially cause a concussion. The processing element 22 may perform the same statistical calculations discussed above for the creation of the profile on head and body movements that are normal, voluntary, non-injurious, and non-concussion-inducing. Every time the user engages in motion that does not exceed the DCT, the measured samples may be used by processing element 22 to update the statistical values, such as the mean, $\mu$, and standard deviation, $\sigma$, in each cell of the profile. That is, the processing element 22 recalculates the mean to be the mean of all of the historically-collected measured samples of the profile and the current corresponding measured sample if it is less than the corresponding DCT. For example, if the first measured sample (received after the processing element 22 has determined that a period of motion has begun) is less than the first array cell DCT, then the processing element 22 recalculates the mean and the standard deviation of the first array cell of the profile to include the current measured sample Likewise for successive measured samples that are less than the DCT. Thus, the profile adapts over time or as certain events or milestones occur, such as the user becoming more proficient at the sport, gaining or losing weight, or otherwise changing his normal pattern of motion. Since the dynamic concussion threshold DCT is computed based on this profile via the formula DCT(n)=μ(n)+SF×σ(n), DCT may also adapt accordingly. This feature may be particularly useful if the device 10 originally includes a general population profile, because over time, the profile may become personalized to the user.

The device 10 may also transmit the real-time measured data from the first and second sensors 12, 14 to a central computer server or a cloud memory or computing mechanism. The server or the cloud may execute a software application which performs additional statistical calculations in order to build a population profile over a plurality of device 10 from a plurality of users. Thus, the profile created by the server may include a general population profile. In certain instances, the software application may create population profiles that are age specific, gender specific, and the like.

Having described the function of device 10, we now describe some additional embodiments.

A second embodiment of the first linkage element 116 is shown in FIG. 8 and may include a first member 128, a second member 132, a bypass element 136, a locking element 138, and a fluid medium 146. The first linkage element 116 may further include first and second end joints which are substantially similar in structure and function to the first and second end joints 30, 34, but are not shown in the figures. The first member 128, the second member 132, and the bypass element 136 may also be substantially similar in structure and function to the first member 28, the second member 32, and the bypass element 36, respectively. Furthermore, a second embodiment of the second linkage element, not shown in the figures, may be substantially similar in structure and function to the first linkage element 116.

The locking element 138 may include a coil 152 of electrically conductive material, such as any one of a plurality of metals known in the art, that is wound around at least a portion of the bypass element 136. The coil 152 is electrically connected to an electric power source 154, such as an electric voltage supply or an electric current supply. In addition, the locking element 138 may include a switching element 156, that when switched to an open state prevents electric current flow to the coil 152, and when switched to a closed state allows electric current flow to the coil 152. When the switching element 156 is in the closed state and electric current is flowing through the coil 152, the coil 152 may generate a magnetic field. Furthermore, the switching element 156 may receive the locking signal from the processing element 22, wherein the locking signal is operable to change the state of the switching element 156.

The fluid medium 146 may include, or be embodied by, a magnetorheological material whose viscosity may be adjusted, or varied, by magnetic field. In a first state, in the absence of a magnetic field, the magnetorheological material may be free flowing and may have a relatively low viscosity. In a second state, in the presence of a magnetic field, the magnetorheological material may have a significantly higher viscosity causing the fluid medium 146 to stop, or nearly stop, flowing.

The first linkage element 116 may operate as follows. When the user is active and experiencing normal, non-concussion-inducing motion, the processing element 22 does not generate the locking signal, and thus, the switching element 156 of the locking element 138 is in the open state, resulting in free flow of the fluid medium 146 and flexible motion of the first linkage element 116. When the user experiences motion from an impact that may potentially cause a concussion, the processing element 22 may detect that the acceleration, for example, is greater than the dynamic concussion threshold for a first period of time and may generate the locking signal. The locking element 138 may receive the locking signal which closes the switching element 156, allowing current flow through the coil 152 which generates a magnetic field and increases the viscosity of the fluid medium 146. Generally, when the processing element generates a locking signal, the viscosity of the magnetorheological material may increase significantly within single digit of ms. At a relatively higher viscosity, the fluid medium 146 stops, or nearly stops, flowing—thereby rendering the first linkage element 116 rigid and locking its position at the approximate time when the locking signal was generated. The processing element 22 may stop generating the locking signal after a short period of time, for example approximately 100 ms to approximately 200 ms. In the absence of the locking signal, the fluid medium 146 no longer receives the magnetic field from the coil 152 and may flow freely—thereby rendering the first linkage element 116 flexible again.

A third embodiment of the first linkage element 216 is shown in FIG. 9 and may include a first member 228, a second member 232, and a locking element 238. The first linkage element 216 may not include a bypass element or a fluid medium. A third embodiment of the second linkage element, not shown in the figures, may be substantially similar in structure and function to the first linkage element 216.

The first member 228 may include a sidewall 240 and a first end wall 242, similar in structure and function to the sidewall 40 and the first end wall 42. The first member 228 may not include a second end wall. The second member 232 may include a rod 248 and a disc 250 with an elongated cylindrical shape and having a plurality or recesses 258, or impressions, distributed axially on a sidewall 260 of the disc 250. Each recess 258 may be oriented in a circumferential direction on the sidewall 260. The locking element 238 may include a solenoid that is coupled to the sidewall 240 of the first member 228. The solenoid may include a movable core or plunger that can be extended into an opening in the sidewall 240 and inserted into one of the recesses 258 on the sidewall 260. The extension of the core may be controlled by the locking signal from the processing element 22.

The first linkage element 216 may operate as follows. When the user is active and experiencing normal, non-concussion-inducing motion, the processing element 22 does not generate the locking signal, and accordingly, the core of locking element 238 solenoid is not extended. The second member 232 of the first linkage element 216 moves freely in a telescoping fashion in and out of the first member 228. When the user experiences motion from an impact that may potentially cause a concussion, the processing element 22 may detect that the acceleration, for example, is greater than the dynamic concussion threshold for a first period of time and may generate the locking signal. The locking element 238 may receive the locking signal and the solenoid may extend its core into one of the recesses of the second member 232, thereby preventing any motion of the second member 232 relative to the first member 228 and rendering the first linkage element 216 rigid. The processing element 22 may stop generating the locking signal after a short period of time, for example approximately 100 ms to approximately 200 ms. In the absence of the locking signal, the core of the locking element 238 solenoid may retract from one of the recesses of the second member 232— thereby allowing free motion of the second member 232 and rendering the first linkage element 216 flexible again.

Figure 10:
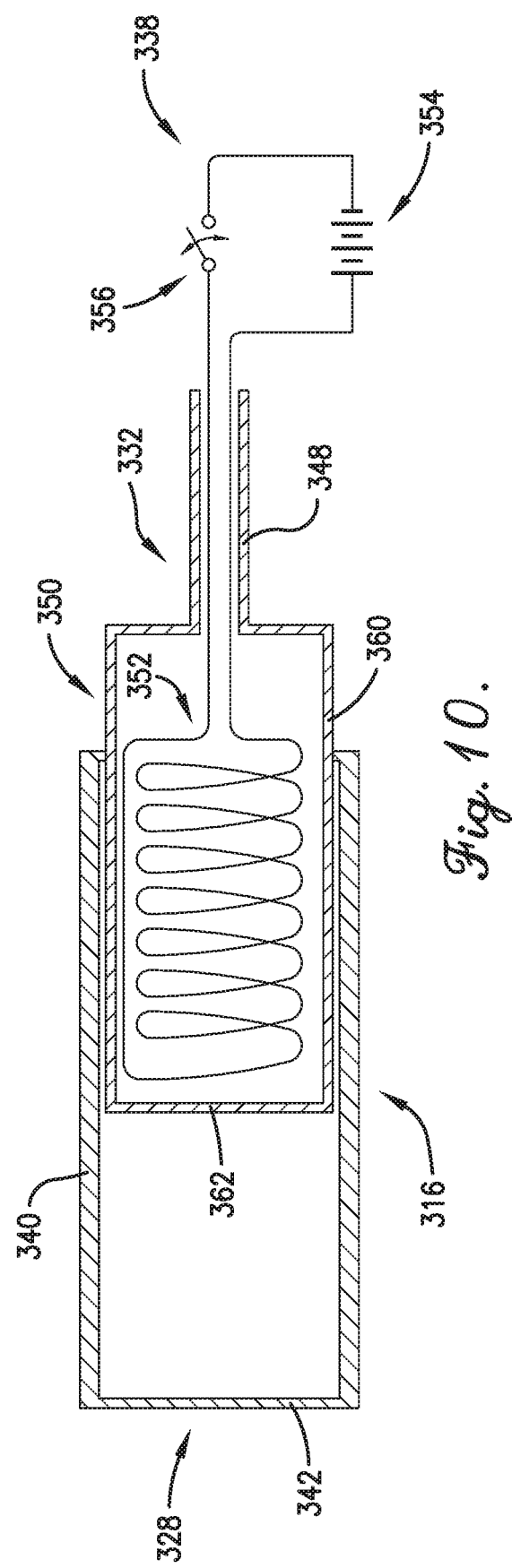
FIG. 10 is a sectional view of a fourth embodiment of the first linkage element.

A fourth embodiment of the first linkage element 316 is shown in FIG. 10 and may include a first member 328, a second member 332, and a locking element 338. A fourth embodiment of the second linkage element, not shown in the figures, may be substantially similar in structure and function to the first linkage element 316.

The first member 328 may include a sidewall 340 and a first end wall 342, similar in structure and function to the first end wall 42 and the sidewall 40, but excluding an end wall. The sidewall 340 may be formed from magnetic material such as iron or steel. The second member 332 may include a rod 348 and a disc 350 with a hollow elongated cylindrical shape and having a sidewall 360 and a first end wall 362. The sidewall 360 may be formed from magnetic material such as iron or steel.

The locking element 338 may include a coil 352, an electric power source 354, and a switching element 356. The coil 352 may be formed from electrically conductive material and may be positioned such that the outer edge of the coil rings is adjacent to an inner surface of the sidewall 360 of the second member 332. The electric power source 354 may include, or be embodied by, an electric voltage supply or an electric current supply. The coil 352 may be electrically connected to the electric power source 354 through the switching element 356, that when switched to an open state prevents electric current flow to the coil 352, and when switched to a closed state allows electric current flow to the coil 352.

The first linkage element 316 may operate as follows. When the user is active and experiencing normal, non-concussion-inducing motion, the processing element 22 does not generate the locking signal, and thus, the locking element 338 is not engaged so that the second member 332 of the first linkage element 316 moves freely in a telescoping fashion in and out of the first member 328. When the user experiences motion from an impact that may potentially cause a concussion, the processing element 22 may detect that the acceleration, for example, is greater than the dynamic concussion threshold for a first period of time and may generate the locking signal. The locking element 338 may receive the locking signal which closes the switching element 356, allowing current flow through the coil 352 which generates a magnetic field and a force of attraction. The attractive force from the coil 352 attracts electromagnetically the sidewall 360 of the second member 332 and the sidewall 340 of the first member 328, which generally stops the relative motion of the two members 328, 332 and renders the first linkage element 316 rigid. The processing element 22 may stop generating the locking signal after a short period of time, for example, approximately 100 ms to approximately 200 ms. In the absence of the locking signal, the coil 352 no longer generates the attractive force, which allows the first and second members 328, 332 to move freely and renders the first linkage element 316 flexible again.

Having described a number of additional embodiments, we now describe some relevant processes of the device 10.

Figure 11:
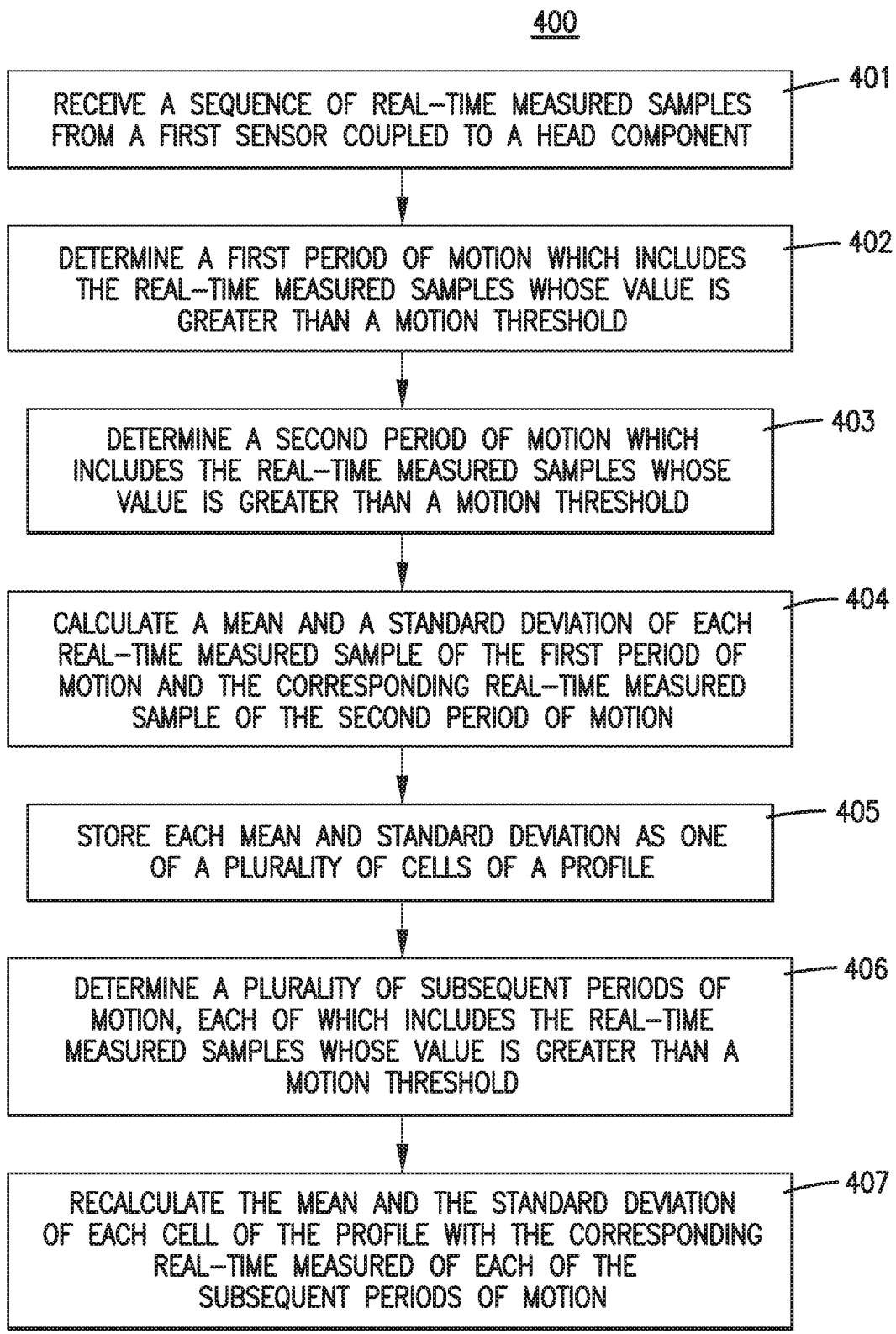
FIG. 11 is a flow diagram of at least a portion of the steps of a method for creating a profile to be used with a device for reducing traumatic brain injury in accordance with another embodiment of the current invention.

At least a portion of the steps of a method 400 for creating a profile of the normal, non-injurious head and body movement of the user to be used with a device for reducing traumatic brain injury, in accordance with another embodiment of the current invention, is shown in FIG. 11. The steps may be performed in the order presented in FIG. 11, or they may be performed in a different order. In addition, some of the steps may be performed simultaneously instead of sequentially. Furthermore, some steps may not be performed. At least a portion of the steps listed are performed by a processing element 22 of the device 10.

Referring to step 401, a sequence of real-time measured samples is received from a first sensor 12 coupled to a head component 24. The first sensor 12 may include one or more components capable of measuring one or more parameters, such as acceleration, along one or more axes or directions, such as pitch, roll, and yaw. The head component 24 may be worn on a user's head and may include or be embodied by an American football helmet. The first sensor 12 may be positioned in the interior of the helmet and may generate the real-time measured samples at an exemplary frequency ranging from 500 hertz (Hz) to 20 kilohertz (kHz) or higher. The second sensor 14 and the body component 26 may be substantially similar. Alternatively, the sensor stage or the smart head-impact-monitoring system of the present invention can be deployed without a head component 24, a body component 26, a first linkage element 16A, and a second linkage element 16B. In this configuration, such as in soccer players, the first sensor 12 may also be integrated into a head-band or a skull-cap or other wearable fabric in order to allow the sensing of head movement and accelerations.

Referring to step 402, a first period of motion, as indicated in FIG. 6, is determined, wherein the first period of motion includes the real-time measured samples, $S1(n)$, whose value is greater than a motion threshold. For example, if the sampling frequency of the sensor stage or the smart head-impact-monitoring system of the present invention is set at 1 kHz, $S1(0)$ is the real-time measured data sampled at 0 ms, $S1(1)$ is the real-time measured data sampled at 1 ms, and so on. The value of each real-time measured sample may be compared, using the processing element 22, to the motion threshold, a constant whose value indicates that the user is moving. The first sample of the stream of real-time measured samples that is greater than the motion threshold becomes the first sample of the first period of motion. The subsequent real-time measured samples whose values are greater than the motion threshold may also be included in the first period of motion. The last real-time measured sample whose value is greater than the motion threshold is the last sample of the first period of motion.

Referring to step 403, a second period of motion, as indicated in FIG. 6, is determined, wherein the second period of motion occurs in time after the first period of motion and includes the real-time measured samples, $S2(n)$, whose value is greater than the motion threshold.

Referring to step 404, a mean, $\mu$, and a standard deviation, $\sigma$, are calculated for each real-time measured sample of the first period of motion and the corresponding real-time measured sample of the second period of motion. For example, referring to FIG. 6, the processing element 22 may calculate $\mu(0)$ as the mean of $S1(0)$, $S2(0)$, etc. and $\sigma(0)$ as the standard deviation of $S1(0)$, $S2(0)$, etc. The subsequent values of $\mu$ and $\sigma$ are calculated in the same fashion using the subsequent values of 51 and S2.

Referring to step 405, the mean, $\mu(n)$, and standard deviation, $\sigma(n)$, are stored as one of a plurality of cells of a profile. For example, as shown in FIG. 6, the first cell of the profile includes $\mu(0)$ and $\sigma(0)$, the second cell of the profile includes $\mu(1)$ and $\sigma(1)$, and so forth.

Referring to step 406, a plurality of subsequent periods of motion are determined. Each subsequent period of motion is determined in the same fashion as described above. The subsequent periods of motion may occur during one or more active outings of the user.

Referring to step 407, the mean, $\mu(n)$, and standard deviation, $\sigma(n)$, for each cell of the profile are recalculated using the corresponding real-time measured sample of the each of the subsequent periods of motion. For example, during a current period of motion, new values of $\mu(0)$ and $\sigma(0)$ are calculated, by the processing element 22, using S(0) from the current period of motion, such that $\mu$ and $\sigma$ represent the mean and standard deviation, respectively, of the first real-time measured samples of all the periods of motion that have occurred up to that point. The calculations are repeated for all of the other cells of the profile. The creation of the profile of the normal, non-injurious head and body movement of the user may be complete once the statistical validity of the profile is established, with values of values of $\mu(n)$ and $\sigma(n)$ becoming invariant even when more real-time measured samples are added to the profile. The completion of the creation of the profile can be detected by the sensor stage or the smart head-impact-monitoring system of the present invention and should occur after a certain number of periods of motion, such as 1,000, have been experienced by the user, or a certain amount of time, such as one or two months, have elapsed.

Figure 12:
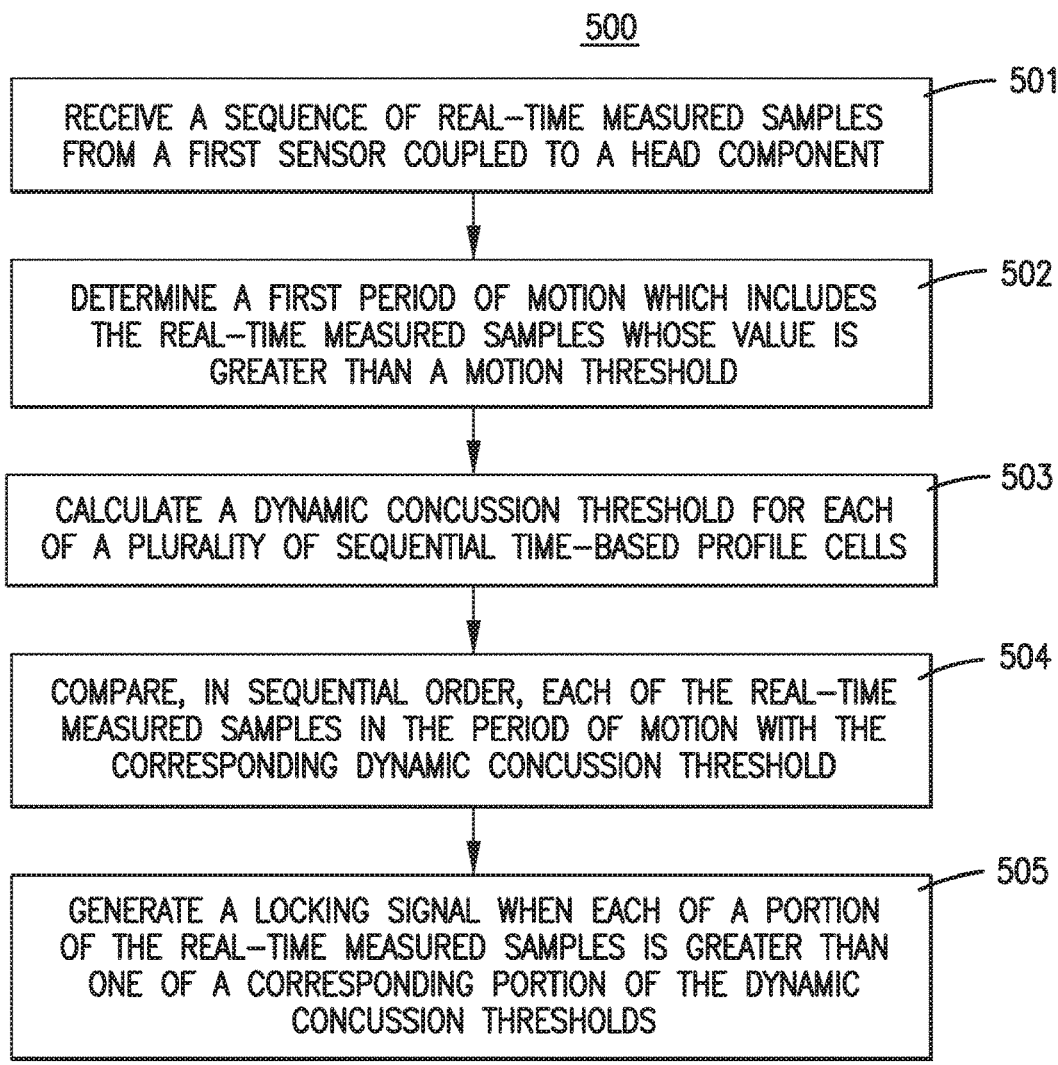
FIG. 12 is a flow diagram of at least a portion of the steps of a method for reducing traumatic brain injury in accordance with yet another embodiment of the current invention.

Once the profile of the normal, non-injurious head and body movement of the user is established, the sensor stage or the smart head-impact-monitoring system of the present invention is switched from a calibration mode to its normal functional mode. In the normal functional mode, at least a portion of the steps of a method 500 for reducing traumatic brain injury, in accordance with yet another embodiment of the current invention, is shown in FIG. 12. The steps may be performed in the order presented in FIG. 12, or they may be performed in a different order. In addition, some of the steps may be performed simultaneously instead of sequentially. Furthermore, some steps may not be performed. At least a portion of the steps listed are performed by a processing element 22 of the device 10.

Referring to step 501, a sequence of real-time measured samples is received from a first sensor 12 coupled to a head component 24. The first sensor 12 may include one or more components capable of measuring one or more parameters, such as acceleration, along one or more axes or directions, such as pitch, roll, and yaw. The head component 24 may be worn on a user's head and may include or be embodied by an American football helmet. The first sensor 12 may be positioned in the interior of the helmet and may generate the real-time measured samples at an exemplary frequency ranging from 500 hertz (Hz) to 20 kilohertz (kHz) or higher. The second sensor 14 and the body component 26 may be substantially similar.

Referring to step 502, a period of motion, as indicated in FIG. 7, is determined, wherein the period of motion includes the real-time measured samples whose value is greater than a motion threshold. The value of each real-time measured sample may be compared, using the processing element 22, to the motion threshold, a constant whose value indicates that the user is moving. The first sample of the stream of real-time measured samples that is greater than the motion threshold becomes the first sample, S(0), of the period of motion. The subsequent real-time measured samples whose values are greater than the motion threshold may also be included in the period of motion. The last real-time measured sample whose value is greater than the motion threshold is the last sample of the period of motion.

Referring to step 503, a plurality of dynamic concussion thresholds is calculated, one for each of a plurality of sequential time-based profile cells. The profile, as indicated in FIG. 7, generally defines, or quantifies, motion by the user that will likely not lead to a concussion and comprises a plurality of cells, each cell including statistical calculations of real-time measured samples from previous periods of motion. Exemplary statistical calculations include a mean, $\mu$, and a standard deviation, $\sigma$, for each cell. In addition, the order of the cells in the profile corresponds to the order of the real-time measured samples in each of the periods of motion used to develop the profile. Each dynamic concussion threshold, DCT, is calculated as, for example, a sum of the mean and the standard deviation multiplied by a sensitivity factor for one of the cells of the profile. The sensitivity factor is determined appropriately according to the dynamic neck stiffness, which is being monitored in real time as the ratio of the data from sensor 12 and sensor 14 as described earlier.

Referring to step 504, each of the real-time measured samples in the period of motion is compared, in sequential order, with the corresponding dynamic concussion threshold. The processing element 22 may compare the first real-time measured sample of the period of motion with the dynamic concussion threshold calculated using the data from the first cell of the profile. The processing element 22 may then compare all the subsequent real-time measured samples with the dynamic concussion thresholds calculated using the data of the subsequent cells. This process is indicated in FIG. 7 as a sequence of decision blocks including: S(0)>DCT(0)?; S(1)>DCT(1)?; S(2)>DCT(2)?; etc.

Referring to step 505, a locking signal is generated when each of a portion of the real-time measured samples is greater than one of a corresponding portion of the dynamic concussion thresholds. The processing element 22 may compare each real-time measured sample of the period of motion with the dynamic concussion threshold calculated from the corresponding profile cell in sequential order. If the processing element 22 determines that a certain number of consecutive samples (representing a first period of time) are greater than the corresponding dynamic concussion thresholds, then the real-time measured samples may indicate the beginning of an impact that could lead to a concussion. It may be that approximately 5-7 ms worth of real-time measured samples that are greater than their corresponding dynamic concussion thresholds is sufficient to mark the beginning of a concussion-causing impact. It may be that more than 5-7 ms worth of real-time measured samples is required. The processing element 22, however, does not wait any longer than 20-30 ms to generate the locking signal so that the linkage elements 16A and 16B can assume their rigidity before a concussion may start or take place. The locking signal may be embodied by an electrical voltage, an electrical current, or another electrical parameter, or a binary data stream, a binary code, or the like. The locking signal may be generated, activated, or asserted for a range from approximately 100 ms to approximately 200 ms. Then, the locking signal is deactivated or deasserted.

Figure 13:
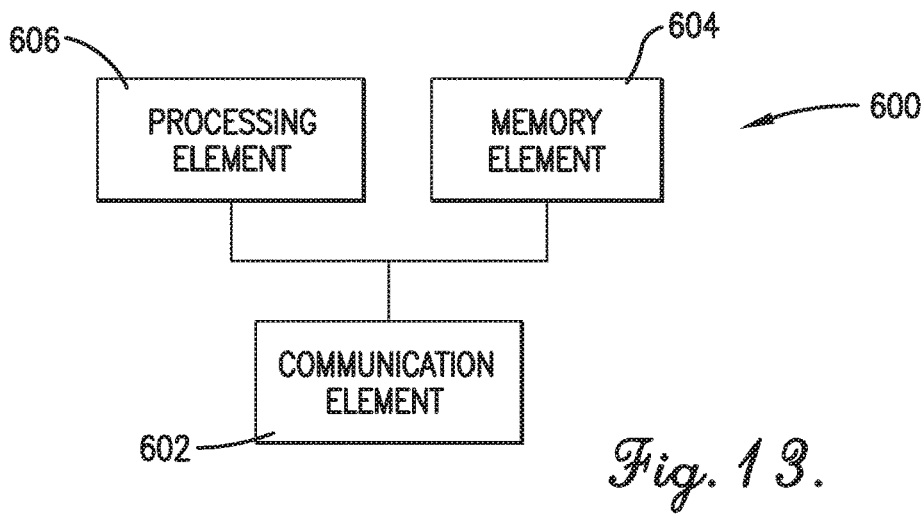
FIG. 13 is a schematic block diagram of at least some of the components of an electronic device configured to control the operation of a device for reducing traumatic brain injury.

An electronic device 600, constructed in accordance with other embodiments of the current invention, for controlling the operation of a device for reducing traumatic brain injury is shown in FIG. 13. The electronic device 600 may broadly comprise a communication element 602, a memory element 604, and a processing element 606. The communication, memory, and processing elements 602, 604, 606 may each be substantially similar in structure and function to the like-named components 18, 20, 22, respectively, discussed above. The electronic device 600 may be utilized for controlling the operation of a device such as the device 10 discussed above. The electronic device 600 may thus be in electronic communication with the first sensor 12, the second sensor 14, and the locking element 38.

Among other functions, the electronic device 600 may perform the following. The processing element 606 may receive the measured samples from the sensors 12, 14, may compare the measured samples with the motion threshold, and may perform the following steps while the measured samples are greater than the motion threshold. The processing element 606 may calculate a plurality of dynamic concussion thresholds, with each dynamic concussion threshold being associated with one of a plurality of sequential, time-based array cells. Each array cell may include a mean and a standard deviation of historically-collected measured samples from the first sensors 12, 14, such that each dynamic concussion threshold is calculated as a sum of the mean and the standard deviation for the associated array cell with the standard deviation multiplied by a sensitivity factor. The sensitivity factor is determined appropriately according to the DNS which is monitored in real time as the ratio of the output data from sensor 12 and sensor 14. The processing element 606 may compare successive sequences of measured samples with successive sequences of dynamic concussion thresholds. The processing element 606 may also generate the locking signal when each measured sample of one of the sequences of measured samples is greater than the corresponding dynamic concussion threshold of a corresponding sequence of dynamic concussion thresholds.

Furthermore, each sequence of measured samples includes a plurality of sequentially-recorded measured samples, S(n). The sequence of measured samples may start with a first measured sample and end with a last measured sample and each successive sequence starts with a next measured sample after the first measured sample of the previous sequence and ends with a next measured sample after the last measured sample of the previous sequence. This creates a moving window of measured samples, wherein the window forms a sequence and each sequence includes the same number of measured samples. For example, if each sequence of measured samples includes ten samples, then a first sequence may include the measured samples: S(0), S(1), . . . , S(9). A second sequence may include the measured samples: S(1), S(2), . . . , S(10). A third sequence may include the measured samples: S(2), S(3), . . . , S(11). And so forth.

Each sequence of dynamic concussion thresholds includes a plurality of sequentially-calculated dynamic concussion thresholds, DCT(n), starting with a first dynamic concussion threshold and ending with a last dynamic concussion threshold and each successive sequence starts with a next dynamic concussion threshold after the first dynamic concussion threshold of the previous sequence and ends with a next dynamic concussion threshold after the last dynamic concussion threshold of the previous sequence. This creates a moving window of dynamic concussion thresholds, wherein the window forms a sequence and each sequence includes the same number of dynamic concussion thresholds. For example, if each sequence of dynamic concussion thresholds includes ten values, then a first sequence may include the values: DCT(0), DCT(1), . . . , DCT(9). A second sequence may include the values: DCT(1), DCT(2), . . . , DCT(10). A third sequence may include the values: DCT(2), DCT(3), . . . , DCT(11). And so forth.

When sequences of measured samples are compared to sequences of dynamic concussion thresholds, the first sequence of measured samples may be compared to the first sequence of dynamic concussion thresholds, wherein S(0) is compared to DCT(0), S(1) is compared to DCT(1), and so forth until S(9) is compared to DCT(9)—assuming each sequence includes ten samples or values. The second sequence of measured samples may be compared to the second sequence of dynamic concussion thresholds, wherein S(1) is compared to DCT(1), S(2) is compared to DCT(2), and so forth until S(10) is compared to DCT(10). The third sequence of measured samples may be compared to the third sequence of dynamic concussion thresholds, wherein S(2) is compared to DCT(2), S(3) is compared to DCT(3), and so forth until S(11) is compared to DCT(11). And so forth. When the measured samples are greater than the values of the dynamic concussion threshold for an entire sequence, then the processing element 606 may generate the locking signal.

Having described the detailed descriptions of the major features of the present invention, we now describe the major utility aspects of the present invention which will lead to some of the claims of the present invention.

Concussions are consequences of inopportune and inappropriate interactions between an impact force and the head. We recognize that the encounter is inopportune as it often occurs when the impact force caught the head-and-neck in a moment of little or no stiffness such that the bulk of the impact force must be dissipated in the head and the brain rather than the body or the trunk. The accurate assessment of the consequences of such interactions, e.g. whether such interactions are concussive or asymptomatic, have so far resisted the advances of technology in head-impact measurement devices [O'Connor et al, Journal of Athletic Training, 52 (3) 206-227, doi 10.4085/1062-6050.52.2.05] but are clearly dependent upon the magnitude and the directionality of the impact force as well as the biomechanical properties of the head-and-neck of the person at the moment of the impact. While it is obvious that one needs to measure the external impact force in order to assess the risk of a concussion, it is not obvious that how one identifies the most salient parameters among the many three-dimension, biomechanical properties of the head-and-neck of the person, including the neck stiffness. It is not obvious as to how to identify and then devise methods to measure such parameters in individuals in order to systematically and accurately assess the risk of the external impact force to the individuals whether they are children, adolescents, or adults. It is not obvious to assign different risks dependent upon whether impact forces are coming from pitch, roll, or yaw axes because the concussion threshold of the human head-and-neck are anisotropic. All of these factors contribute to the difficulty why It is not obvious to somehow predict that the luck is about to run out and some inopportune event is to occur. The present invention addresses these challenges. That the solutions to these problems are not obvious has been made clear by the comprehensive 2017 review article of O'Connor et al.

First, the human head-and-neck is intrinsically anisotropic. After conducting a series of studies, we recognized that the thresholds of concussive injuries are dramatically different among the three degree of rotational freedom of the head-and-neck—pitch, roll, and yaw. Embodiments of the current invention include a pitch-roll-yaw analysis to assess impact forces in components along the pitch, roll, and yaw axes.

Second, the biomechanical properties of the head-and-neck of each person are different and are personalized. We recognized that the patterns or profiles of normal and non-injurious head and body movements and those that are abnormal and potentially injurious are related to one another and are also related to the biomechanical properties of the head-and-neck of the user. The first is knowable and the second is possibly knowable. We recognize that we can implement machine learning (without being specifically programmed with that information) in order to gain knowledge on the user's profile of normal and non-injurious head and body movements. This profile is then used as a yard stick to gauge the range of normal movement parameters that is well tolerated by the user's head-and-neck expressed in head movement parameters such as position, orientation, velocity, acceleration, and so on, paying particular attention to the components of these parameters along the axes of pitch, roll, and yaw. From this profile, the processing element 22 derives personalized dynamic concussive thresholds (DCT) in pitch, roll, and yaw axes with additional information on the dynamic neck stiffness (DNS) of the user monitored in real time, also measured in pitch, roll, and yaw axes whether the users may be children, adolescents or adults.

Third, we recognized that a particular head impact event is inopportune often because the impact caught the head-and-neck in a state of low stiffness. The output of MEMS devices such as an accelerometer chip to an external force is determined by f=ma where m is the effective mass of the head, which, in turn, is a function of the individualized biomechanical properties of the head-and-neck, chief among them is the mass of the head, mass of the body, and the neck stiffness. At the moment of impact, therefore, the neck stiffness influences the physics of impact force/energy dissipation to the head vs. the body, whether too much energy/force is dissipated to the head to cause injuries, and importantly, the very numbers as the output of the MEMS sensors indicating force or acceleration. A plausible solution to improve the sensitivity and specificity of the MEMS devices may be to address the individualized concussion threshold and the neck stiffness. Embodiments of the current invention include the use of multiple sensors to construct a system of sensor to measure the neck stiffness DNSI, a parameter closely related to neck stiffness and critical to the rendering of protective countermeasure aimed at providing additional neck stiffness. We then injected DNSI directly into the equation that determines DCT.

Fourth, although protective countermeasure (such as providing additional neck stiffness) can only be launched after the detection of a potentially injurious head-impact event, we recognized that such countermeasure must be launched before the concussion injuries occur. Embodiments of the current invention include the use of fast algorithms as well as fast-acting mechanical devices to satisfy these requirements.

Although the invention has been described with reference to the embodiments illustrated in the attached drawing figures, it is noted that equivalents may be employed and substitutions made herein without departing from the scope of the invention as recited in the claims.

Having thus described the invention, what is claimed as new and desired to be secured by Letters Patent is:

1. A system for reducing traumatic brain injury, the system comprising:
   a first sensor coupled to a head component configured to measure accelerations of a head of a subject;
   a second sensor coupled to a body component configured to measure accelerations of a body of the subject;
   a linkage element configured to connect said head component to said body component, said linkage element switchable between a first, flexible state and a second, rigid state;
   a processor configured to receive signal data from said first sensor and from said second sensor;
   said processor further configured to calculate a plurality of positional values based upon said signal data to indicate various components of rotational acceleration of the head and various components of rotational acceleration of the body;
   said processor further configured to calculate a plurality of baseline values from said signal data to distinguish normal, voluntary head and body movements from impact-induced head and body movements;
   said processor further configured to calculate a plurality of NSI values from said signal data to indicate neck stiffness indexes (NSI);
   said processor further configured to derive from the NSI values as compared with said positional values and said baseline values as one of a plurality of warning signals for a potential concussive event; and
   said processor further configured to generate a locking signal to said linkage element based on the warning signals, thereby transforming said linkage element from said flexible state to said rigid state.

2. The system of claim 1, further comprising:
   wherein said head component comprises a helmet; and
   wherein said neck component comprises an article configured to be worn about the neck and shoulders of the subject.

3. The system of claim 1, wherein said linkage element comprises a pair of telescoping arms.

4. The system of claim 1, further comprising:
   said processor further configured to constantly receive data streaming from said first and second sensors;
   said processor further configured to identify periods of head movement events from the streaming data based upon when the data sent by said first and second sensors contain non-zero values of head and body accelerations indicating movement thereof, with non-zero defined as above instrument noise level of said first and second sensors;
   said processor further configured to identify a beginning of a single head or body movement event when a plurality of non-zero head or body accelerations occur in succession and assume progressively larger acceleration values; and
   said processor further configured to distinguish impact-induced head and body movement events from normal, voluntary head and body movements by comparing time-dependent signatures of impact-induced and normal, voluntary head and body movement events against said single head or body movement event.

5. The system of claim 1, further comprising: said processor further configured to calculate a three orthogonal components of rotational acceleration of the head during a movement event from data sent by said first and second sensors, said three orthogonal components of rotational acceleration comprising pitch, roll, and yaw; said processor further configured to compile data on said three orthogonal components of rotational accelerations of the head and the body as a plurality of time series of acceleration data with time stamps according to an internal clock of the processor for a purpose of identifying a series of acceleration data associated with a given movement event which is in turn identified by said processor by an exact time when the movement event begins; said processor further configured to identify a maximal value within said time series of acceleration data collected during a given movement event for each of the three orthogonal components of rotational acceleration of the head and the body; and said processor further configured to store said time series data on various components of rotational acceleration data of the head and the body in a memory of the processor as a series of acceleration data with time stamps for the purpose of identifying the acceleration data with the movement event.

6. The system of claim 1, further comprising:
said processor further configured to calculate a neck stiffness index NSIP as a quotient of body rotational acceleration component in pitch as measured by said second sensor and divided by head rotational acceleration component in pitch as measured by said first sensor;
said processor further configured to calculate a neck stiffness index NSIR as the quotient of body rotational acceleration component in roll as measured by said second sensor divided by head rotational acceleration component in roll as measured by said first sensor;
said processor further configured to calculate a neck stiffness index NSIY as the quotient of body rotational acceleration component in yaw as measured by said second sensor divided by head rotational acceleration component in yaw as measured by said first sensor;
said processor further configured to recalculate said neck stiffness index NSI as the vectorial sum of NSIP, NSIR, and NSIY;
said processor further configured to process said NSI as a time series of data points with time stamps for a purpose of identifying the neck stiffness index NSI data with an impact-induced movement event;
said processor further configured to identify a minimal value of NSI from the time series of data points with time stamps to identify a minimal NSI with an impact-induced movement event; and
said processor further configured to store data on various components of neck stiffness index data points in a memory of the processer as a time series of data points with time stamps for the purpose of identifying the neck stiffness NSI index data with an impact-induced movement event.

7. The system of claim 1, further comprising:
said processor configured to measure and determine three orthogonal components of NSI;
said processor further configured to compare minima of said three orthogonal components of NSI to compare an impact-induced movement event to a set of predetermined thresholds; and
said processor further configured to generate the warning signals for the concussive event when said comparison indicates one of the minima of the three orthogonal components of NSI is less than a set of predetermined thresholds and further configured to thereby generate the locking signal for said linkage elements.

8. The system of claim 6, further comprising:
said processor further configured to calculate a maxima maximum in each of the time series of three orthogonal components of rotational acceleration of the head and the body for a given movement event in a same coordinate system as that in specifying the various components of the neck stiffness index NSI;
said processor further configured to compare said maximum on rotational acceleration of the head and the body to a set of predetermined thresholds;
said processor further configured to generate the warning signal among the plurality of warning signals for the concussive event when the one of said maximum on rotational acceleration of the head and the body exceeds said predetermined threshold; and said processor further configured to generate the locking signal to the linkage elements when the one of said maximum on rotational acceleration of the head and the body exceeds said predetermined threshold.

9. A system for reducing traumatic brain injury, the system comprising:
a first sensor coupled to a head component configured to measure a subject's head accelerations;
a second sensor coupled to a body component configured to measure accelerations of the subject's body;
a linkage element configured to connect said head component to said body component, said linkage element switchable between a first, flexible state and a second, rigid state; a processor configured to receive data from said first sensor and said second sensor; said processor further configured to calculate a plurality of values to indicate various components of rotational accelerations of the head and the body in a movement event in a same coordinate system as that in specifying the various components of a neck stiffness index NSI;
said processor further configured to derive from values of said various components of rotational accelerations of the head and the body in the movement event as one of a plurality of warning signals for a potential concussive event; and said processor further configured to generate a locking signal to the said linkage element based on the said warning signals, thereby transforming said linkage element from said first, flexible state to said second, rigid state.

10. A system for reducing traumatic brain injury, the system comprising: a first sensor coupled to a head component to measure a subject's head accelerations;
a second sensor coupled to a body component configured to measure accelerations of the subject's body;
a linkage element configured to connect said head component to said body component, said linkage element switchable between a first, flexible state and a second, rigid state; a processor configured to receive data from said first sensor and from said second sensor;
said processor further configured to calculate a plurality of values to indicate personalized concussive thresholds in a coordinate system corresponding with a neck stiffness index NSI; said processor further configured to generate a warning signal for a concussive event when said sensors detect accelerations exceeding said personalized concussive threshold; and said processor further configured to generate a locking signal to the said linkage element thereby transforming said linkage element from said first, flexible state to said second, rigid state.

11. The system of claim 10, further comprising: said processor further configured to calculate a plurality of values on a maximal rotational acceleration of the head and the body for each head or body movement event in the same coordinate system as that in specifying various components of the neck stiffness index NSTI;
said processor further configured to compile a plurality of data files containing values of the said maximal rotational accelerations of the head and the body for a plurality of head and body movement events in order to provide a representation of historical, normal, non-injurious head and body movement events;
said processor further configured to calculate and derive statistical information such as mean and standard deviation of the maximal rotational accelerations of the head and the body for a plurality of head and body movement events;

said processor further configured to display graphically a dot pattern on the historical, normal, non-injurious head and body movement events as a collection of dots each of which is a data points in three-dimension space of pitch, roll, and yaw with a coordination of the data points being the values of the maximal rotational accelerations of the head and the body in acceleration units for a given head or body movement events; said processor further configured to define a first volume occupied by the historical, normal, non-injurious head and body movement events in three-dimension in said pitch-roll-yaw space; said processor further configured to display a second volume occupied by potentially injurious head or body movement as a space outside of the volume occupied by the historical, normal, non-injurious head and body movement events in said pitch-roll-yaw space; said processor further configured to define a first data range occupied potentially injurious head or body movement events as the data range outside a second data range occupied by the historical, normal, non-injurious head and body movement events in statistical terms such as mean and standard deviations;

said processor further configured to display graphically a boundary between volume occupied by the historical, normal, non-injurious head and body movement events and potentially injurious head or body movement in said pitch-roll-yaw space.

12. The system of claim 10, further comprising:
said processor further configured to compile incoming acceleration data from said first sensor and said second sensor to derive boundaries between historical normal, non-injurious head and body movement and potentially injurious head and body movements;

said processor further configured to refresh compiled acceleration data by replacing older data points with newer data points on a first-in-first-out manner (FIFO);
said processor further configured to deposit into a processor memory on a scheduled basis; and
said processor further configured to use a most recently compiled acceleration data for a purpose of generating said personalized concussive thresholds.

13. A system for reducing traumatic brain injury, the system comprising:
a first sensor coupled to a head component configured to measure a subject's head accelerations;
a second sensor coupled to a body component configured to measure accelerations of the subject's body;
a linkage element configured to connect said head component to said body component, said linkage element switchable between a first, flexible state and a second, rigid state upon receiving a locking signal;
a processor configured to receive data from said first sensor and said second sensor;
said processor further configured to calculate a plurality of values to determine a concussive threshold;
said processor further configured to generate the locking signal to said linkage element when said first and second sensors detect accelerations exceeding said concussive threshold transforming said linkage element from said first, flexible state to said second, rigid state; and
said processor further configured to terminate the locking signal to said linkage element after a brief time period such as 100-300 msec after a beginning portion of a head movement event, thereby returning said linkage element from said second, rigid state to said first, flexible state.

* * * * *